(12) United States Patent
Celzard et al.

(10) Patent No.: US 9,994,690 B2
(45) Date of Patent: Jun. 12, 2018

(54) CELLULAR POROUS MONOLITHS CONTAINING CONDENSED TANNINS

(71) Applicants: UNIVERSITE DE LORRAINE, Nancy (FR); CENTRE NATIONAL DE LA RECHERCHE SCIENTIFIQUE, Paris (FR)

(72) Inventors: Alain Celzard, Epinal (FR); Andrzej Szczurek, Villers-les-nancy (FR); Vanessa Fierro, Epinal (FR); Antonio Pizzi, Chantraine (FR)

(73) Assignees: UNIVERSITE DE LORRAINE, Nancy (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 216 days.

(21) Appl. No.: 14/425,074

(22) PCT Filed: Aug. 27, 2013

(86) PCT No.: PCT/EP2013/067716
§ 371 (c)(1),
(2) Date: Jun. 4, 2015

(87) PCT Pub. No.: WO2014/033124
PCT Pub. Date: Mar. 6, 2014

(65) Prior Publication Data
US 2015/0274921 A1 Oct. 1, 2015

(30) Foreign Application Priority Data
Aug. 28, 2012 (FR) ...................... 12 58032

(51) Int. Cl.

| | | |
|---|---|---|
| C08J 9/28 | (2006.01) |
| B01J 20/02 | (2006.01) |
| G10K 11/162 | (2006.01) |
| F16L 59/02 | (2006.01) |
| A61K 47/02 | (2006.01) |
| A61L 27/02 | (2006.01) |
| A61L 27/08 | (2006.01) |
| A61L 27/42 | (2006.01) |
| B01J 37/08 | (2006.01) |
| B01J 20/20 | (2006.01) |
| B01J 20/24 | (2006.01) |
| B01J 20/28 | (2006.01) |
| B01J 20/283 | (2006.01) |
| B01J 20/285 | (2006.01) |
| B01J 20/30 | (2006.01) |
| B01J 21/18 | (2006.01) |
| B01J 27/224 | (2006.01) |
| B01J 31/06 | (2006.01) |
| B01J 35/04 | (2006.01) |
| B01J 37/00 | (2006.01) |
| C08L 97/00 | (2006.01) |
| C08L 91/00 | (2006.01) |
| C08G 8/20 | (2006.01) |
| C08L 61/12 | (2006.01) |

(Continued)

(52) U.S. Cl.
CPC ............ *C08J 9/283* (2013.01); *A61K 47/02* (2013.01); *A61L 27/025* (2013.01); *A61L 27/08* (2013.01); *A61L 27/422* (2013.01); *B01J 20/02* (2013.01); *B01J 20/0251* (2013.01); *B01J 20/20* (2013.01); *B01J 20/24* (2013.01); *B01J 20/283* (2013.01); *B01J 20/285* (2013.01); *B01J 20/28042* (2013.01); *B01J 20/3064* (2013.01); *B01J 21/18* (2013.01); *B01J 27/224* (2013.01); *B01J 31/061* (2013.01); *B01J 35/04* (2013.01); *B01J 37/0018* (2013.01); *B01J 37/084* (2013.01); *C01B 32/05* (2017.08); *C01B 32/956* (2017.08); *C08G 8/20* (2013.01); *C08L 61/12* (2013.01); *C08L 91/00* (2013.01); *C08L 97/00* (2013.01); *F16L 59/028* (2013.01); *G10K 11/162* (2013.01); *A61L 2430/00* (2013.01); *B01J 2220/82* (2013.01); *B01J 2231/005* (2013.01); *B01J 2531/002* (2013.01); *C08J 2201/028* (2013.01); *C08J 2205/10* (2013.01); *C08J 2207/10* (2013.01); *C08J 2399/00* (2013.01)

(58) Field of Classification Search
CPC ............ C08J 9/28; C08J 9/283; C08J 9/286
See application file for complete search history.

(56) References Cited

U.S. PATENT DOCUMENTS

2007/0049887 A1 3/2007 Miura et al.
2008/0161440 A1* 7/2008 Marten .................. C08G 18/12
521/159

FOREIGN PATENT DOCUMENTS

CA 2834600 A1 * 11/2012 ............ C08J 9/0061
EP 0060138 9/1982

OTHER PUBLICATIONS

Michael R. Buchmeiser,"Polymeric Monolithic Materials: Syntheses, Properties, Functionalization and Applications", Polymer, vol. 48, 2007, pp. 2187-2198.
Zhang et al., "Stability of High Internal Phase Emulsions with Sole Cationic Surfactant and its Tailoring Morphology of Porous Polymers based on the Emulsions", Polymer, vol. 50, 2009, pp. 1723-1731.
Tondi et al., "Tannin-Based Carbon Foams", Carbon, vol. 47, 2009, pp. 1480-1492.
Tondi et al., "Tannin-Based Rigid Foams: A Survey of Chemical and Physical Properties, Bioresource Technology", vol. 100, Issue 21, Nov. 2009, pp. 5162-5169.

(Continued)

*Primary Examiner* — Melissa A Rioja
(74) *Attorney, Agent, or Firm* — Greer, Burns & Crain, Ltd.

(57) ABSTRACT

A method for producing polyHIPE porous monoliths, of the polyHIPE type or in the form of a rigid foam, by hardening solutions of condensed tannins in the presence of oil and/or air or in the presence of a non-water-miscible volatile solvent and/or air. Also disclosed is the use of these materials in the areas of catalysis, chromatography, heat and sound insulation, tissue engineering and medication release and as a floral foam.

9 Claims, 22 Drawing Sheets

(51) Int. Cl.
*C01B 32/05* (2017.01)
*C01B 32/956* (2017.01)

(56) References Cited

OTHER PUBLICATIONS

Zhao et al., "Effect of Composition and Processing Parameters on the Characteristics of Tannin-Based Rigid Foams. Part II: Physical Properties", Materials Chemistry and Physics, vol. 123, 2010, pp. 210-217.

Zhao et al., "Effect of Composition and Processing Parameters on the Characteristics of Tannin-Based Rigid Foams. Part I: Cell Structure", Materials Chemistry and Physics, vol. 122, 2010, pp. 175-182.

Basso et al., "Green, Formaldehyde-free, Foams for Thermal Insulation", Advanced Materials Letters, vol. 2, No. 6, 2011, pp. 378-382.

Li et al., "Tailoring the Structure of Cellular Vitreous Carbon Foams", Carbon, vol. 50, 2012, pp. 2026-2036.

Li et al., Chemical Modification of Tannin/Furanic Rigid Foams by Isocyanates and Polyurethanes, Maderas. Ciencia y technologia, vol. 14, No. 3, 2012, pp. 257-265.

Lacoste et al., "Pine Tannin-Based Rigid Foams: Mechanical and Thermal Properties", Industrial Crops and Products, vol. 43, 2013, pp. 245-250.

Forgacz, "Elaboration de materiaux poreux a partir de sous-produits de la biomasse par poilymerisation d'emulsions concentrees" thesis, http://www.theses.fr/2011BOR14435, Dec. 9, 2011.

\* cited by examiner

Figure 1

| Sample | F45A | F75A | F105A |
|---|---|---|---|
| Apparent density of monolith (g/cm$^3$) | 0.192 | 0.176 | 0.155 |
| Skeletal density of monolith (g/cm$^3$) | 1.45 | 1.45 | 1.45 |
| Porosity of monolith (%) | 86.75 | 87.89 | 89.28 |
| Total pore volume of monolith (cm$^3$/g) | 4.52 | 5.00 | 5.76 |
| Young's modulus of monolith (MPa) | 19.22 | 29.96 | 16.13 |
| Compression strength of monolith (MPa) | 0.73 | 1.99 | 1.83 |
| Total intrusion volume of monolith (cm$^3$/g) | 4.41 | 3.80 | 4.96 |
| Specific surface area of monolith (m$^2$/g) | 7.6 | 6.5 | 8.8 |
| Median diameter of pores of monolith (μm) | 10.4 | 2.3 | 2.4 |
| Average diameter of cells of monolith (μm) | 50 | 20 | 30 |

Figure 2
F45A
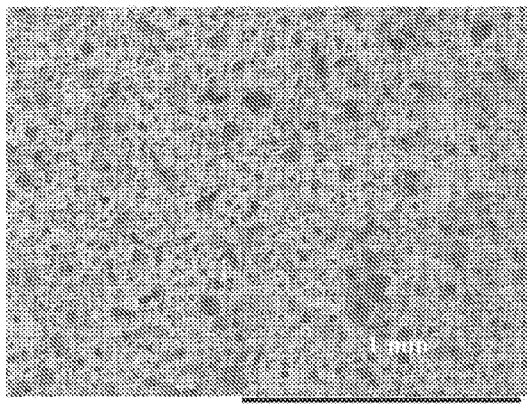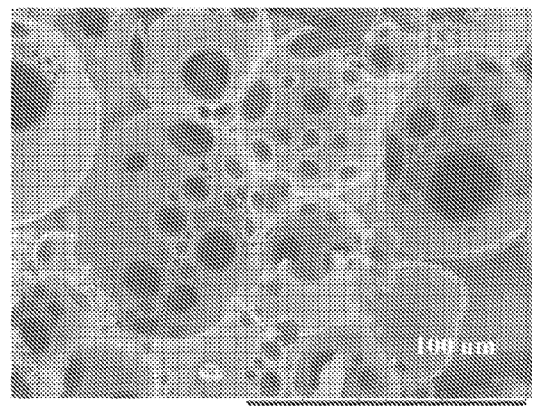
F75A
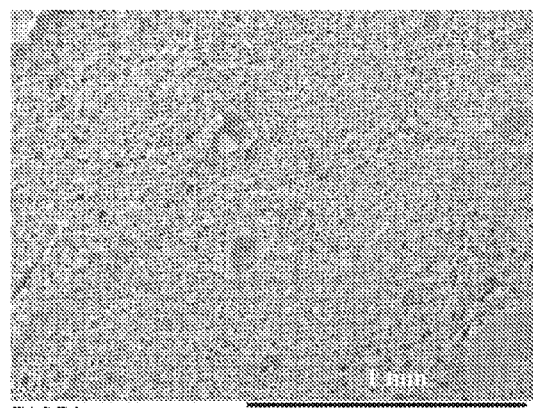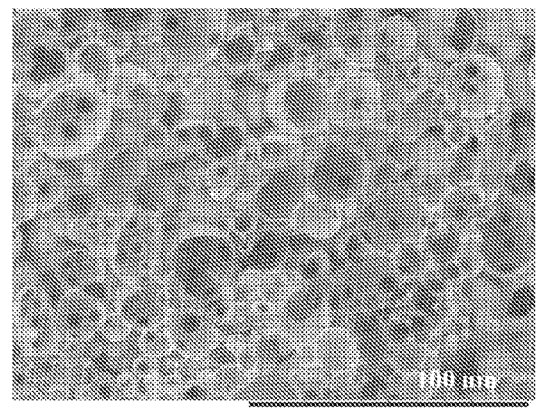
F105A
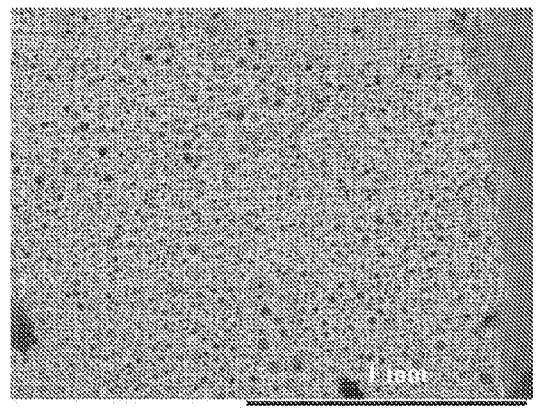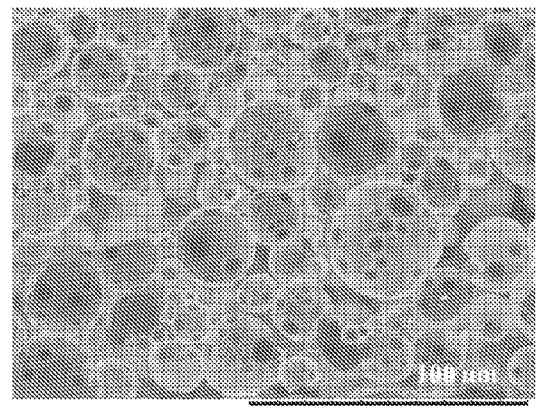

Figure 3

| Sample | F45B | F75B | F105B |
|---|---|---|---|
| Tannin (%/(water +tannin)) | 40 | 40 | 40 |
| Surfactant (%/(water +tannin)) | 2.6 | 2.6 | 2.6 |
| Tannin/oil | 40/45 | 40/75 | 40/105 |
| pH of the tannin solution | 6 | 6 | 6 |
| Rotation speed (rpm) | 250 | 250 | 250 |
| Apparent density of monolith (g/cm$^3$) | 0.210 | 0.185 | 0.142 |
| Skeletal density of monolith (g/cm$^3$) | 1.45 | 1.45 | 1.45 |
| Porosity of monolith (%) | 85.51 | 87.27 | 90.19 |
| Total pore volume of monolith (cm$^3$/g) | 4.07 | 4.72 | 6.35 |
| Young's modulus of monolith (MPa) | 8.76 | 22.36 | 17.18 |
| Compression strength of monolith (MPa) | 0.99 | 0.75 | 0.73 |

Figure 4

| Sample | F30-4-2k | F60-4-2k | F90-4-2k |
|---|---|---|---|
| Apparent density of monolith (g/cm$^3$) | 0.056 | 0.082 | 0.093 |
| Skeletal density of monolith (g/cm$^3$) | 1.45 | 1.45 | 1.45 |
| Porosity of monolith (%) | 96.11 | 94.36 | 93.60 |
| Total pore volume of monolith (cm$^3$/g) | 17.17 | 11.51 | 10.06 |
| Young's modulus of monolith (MPa) | 3.60 | 5.01 | 11.52 |
| Compression strength of monolith (MPa) | 0.16 | 0.21 | 0.52 |

Figure 5
F30-4-2k
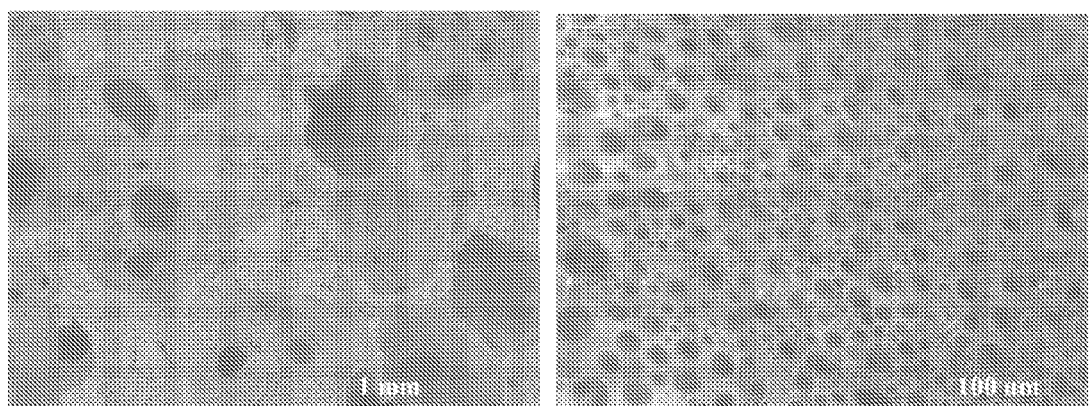
F60-4-2k
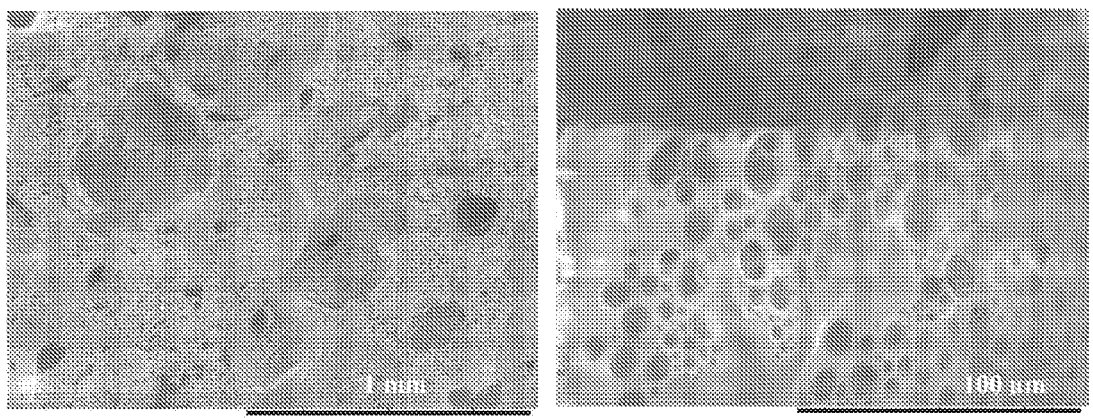
F90-4-2k
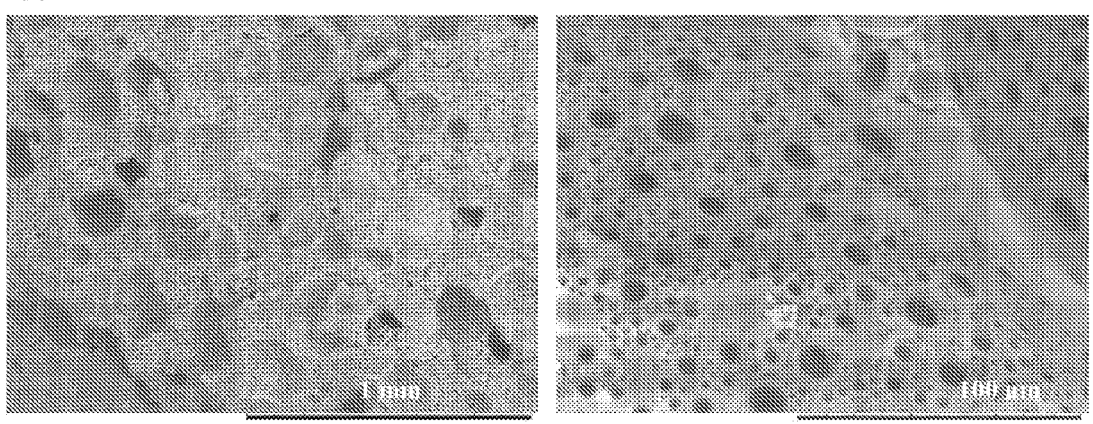

Figure 6

| Sample | F30-6-2k | F60-6-2k | F90-6-2k |
|---|---|---|---|
| Apparent density of monolith (g/cm$^3$) | 0.057 | 0.079 | 0.129 |
| Skeletal density of monolith (g/cm$^3$) | 1.45 | 1.45 | 1.45 |
| Porosity of monolith (%) | 96.08 | 94.56 | 91.09 |
| Total pore volume of monolith (cm$^3$/g) | 16.85 | 11.97 | 7.06 |
| Young's modulus of monolith (MPa) | 3.31 | 7.38 | 15.89 |
| Compression strength of monolith (MPa) | 0.11 | 0.34 | 0.72 |
| Total intrusion volume of monolith (cm$^3$/g) | 11.36 | 9.46 | 5.63 |
| Total surface area of pores of monolith (m$^2$/g) | 6.40 | 9.20 | 7.99 |
| Median diameter of pores of monolith (μm) | 1.12 | 1.36 | 2.76 |

Figure 7

| Sample | F30-8-2k | F60-8-2k | F90-8-2k |
|---|---|---|---|
| Apparent density of monolith (g/cm$^3$) | 0.134 | / | 0.249 |
| Skeletal density of monolith (g/cm$^3$) | 1.45 | / | 1.45 |
| Porosity of monolith (%) | 90.78 | / | 82.82 |
| Total pore volume of monolith (cm$^3$/g) | 6.77 | / | 3.33 |
| Young's modulus of monolith (MPa) | 1.73 | / | 20.01 |
| Compression strength of monolith (MPa) | 0.09 | / | 1.63 |

Figure 8

| Sample | F20-40 | F40-40 | F50-40 |
|---|---|---|---|
| Apparent density of monolith (g/cm$^3$) | 0.020 | 0.098 | 0.179 |
| Skeletal density of monolith (g/cm$^3$) | 1.45 | 1.45 | 1.45 |
| Porosity of monolith (%) | 98.62 | 93.24 | 87.66 |
| Total pore volume of monolith (cm$^3$/g) | 49.31 | 9.511 | 4.90 |
| Young's modulus of monolith (MPa) | 0.09 | 2.99 | 5.41 |
| Compression strength of monolith (MPa) | 0.02 | 0.21 | 0.52 |
| Total intrusion volume of monolith (cm$^3$/g) | / | 9.70 | 4.81 |
| Total surface area of pores of monolith (m$^2$/g) | / | 2.06 | 1.03 |
| Median diameter of pores of monolith (μm) | / | 7.39 | 1.91 |

Figure 9
F20-40
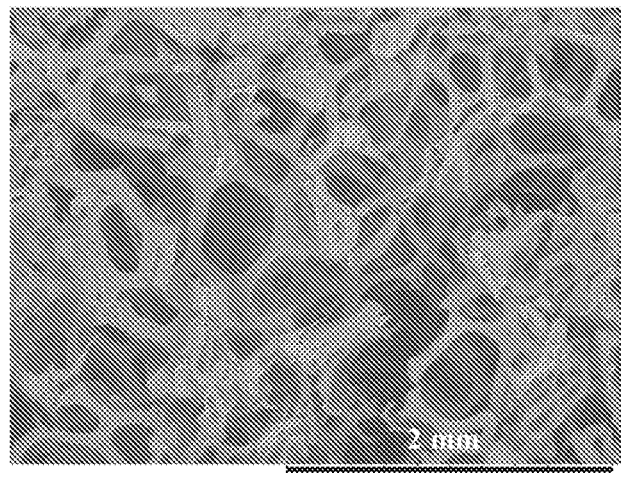
F40-40
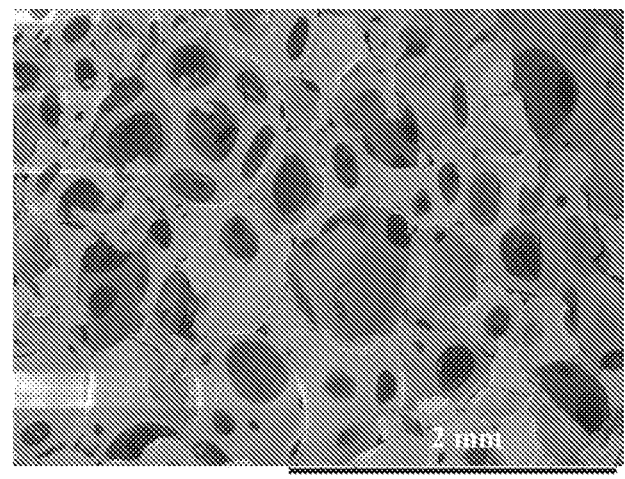
F50-40
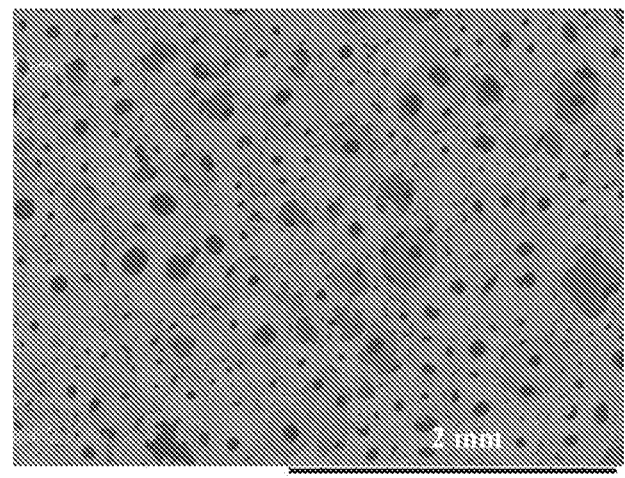

Figure 10

| Sample | CF45A | CF75A | CF105A |
|---|---|---|---|
| Apparent density of monolith (g/cm$^3$) | 0.249 | 0.190 | 0.141 |
| Skeletal density of monolith (g/cm$^3$) | 2.0 | 2.0 | 2.0 |
| Porosity of monolith (%) | 87.53 | 90.52 | 92.93 |
| Total pore volume of monolith (cm$^3$/g) | 3.51 | 4.76 | 6.59 |
| Young's modulus of monolith (MPa) | 45.21 | 74.13 | 102.99 |
| Compression strength of monolith (MPa) | 1.40 | 5.19 | 5.70 |
| Total intrusion volume of monolith (cm$^3$/g) | 3.61 | 4.40 | 6.71 |
| Total surface area of pores of monolith (m$^2$/g) | 5.15 | 8.59 | 6.57 |
| Median diameter of pores of monolith (μm) | 1.10 | 1.63 | 2.37 |

Figure 12

| Sample | CF30-6-2k | CF60-6-2k | CF90-6-2k |
|---|---|---|---|
| Apparent density of monolith ($g/cm^3$) | 0.082 | 0.107 | 0.129 |
| Skeletal density of monolith ($g/cm^3$) | 2.0 | 2.0 | 2.0 |
| Porosity of monolith (%) | 95.92 | 94.65 | 93.54 |
| Total pore volume of monolith ($cm^3/g$) | 11.70 | 8.85 | 7.25 |
| Young's modulus of monolith (MPa) | 8.50 | 19.07 | 49.48 |
| Compression strength of monolith (MPa) | 0.37 | 1.14 | 3.82 |
| Total intrusion volume of monolith ($cm^3/g$) | 11.63 | 8.39 | 6.73 |
| Total surface area of pores of monolith ($m^2/g$) | 16.78 | 15.85 | 27.91 |
| Median diameter of pores of monolith (μm) | 0.25 | 0.45 | 0.82 |

Figure 14

| Sample | TC | TH |
|---|---|---|
| Apparent density (g/cm$^3$)[1] | 0.147 | 0.208 |
| Skeletal density (g/cm$^3$)[2] | 1.413 | 1.420 |
| Porosity (%)[3] | 89.6 | 85.4 |
| Total pore volume (cm$^3$/g)[3] | 6.10 | 4.10 |
| Young's modulus (MPa) | 25.88 | 27.54 |
| Compression strength (MPa) | 0.96 | 1.37 |
| Thermal conductivity (W/m/K) | 0.0557 | 0.0692 |
| Total intrusion volume (cm$^3$/g)[4] | 4.101 | 2.832 |
| Specific surface area (m$^2$/g)[4] | 16.601 | 7.726 |
| Median diameter of pores (μm)[4] | 0.84 | 1.36 |
| Average diameter of pores (μm)[4] | 0.99 | 1.47 |

[1] Determined by weighing cylindrical samples of known dimensions
[2] Determined by helium pycnometry
[3] Determined from measurements 1 and 2
[4] Determined by mercury porosimetry Figure 15
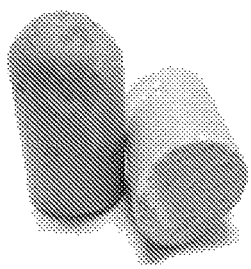  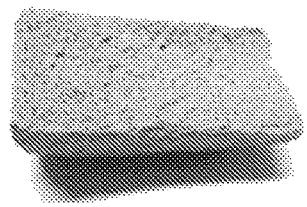  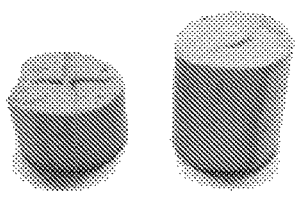
Cyclohexane         Heptane              Sunflower oil

Figure 16

| Sample | Tween 80 |
|---|---|
| Apparent density (g/cm$^3$)$^1$ | 0.094 |
| Skeletal density (g/cm$^3$)$^2$ | 1.41 |
| Porosity (%)$^3$ | 93.34 |
| Total pore volume (cm$^3$/g)$^3$ | 9.93 |
| Young's modulus (MPa) | 7.91 |
| Compression strength (MPa) | 0.36 |
| Thermal conductivity (W/m/K) | 0.0588 |
| Total intrusion volume (cm$^3$/g)$^4$ | 6.94 |
| Specific surface area (m$^2$/g)$^4$ | 0.84 |
| Median diameter of pores (μm)$^4$ | 12.26 |
| Average diameter of pores (μm)$^4$ | 33.24 |

[1] Determined by weighing cylindrical samples of known dimensions
[2] Determined by helium pycnometry
[3] Determined from measurements 1 and 2
[4] Determined by mercury porosimetry Figure 17
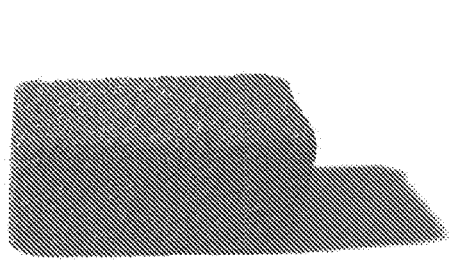 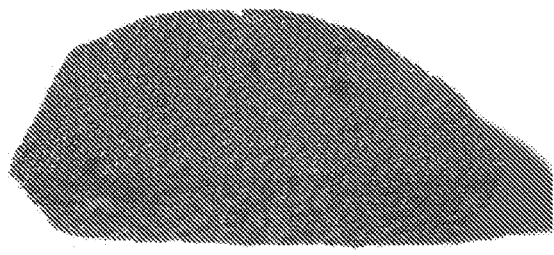
Pluronic 6800  Tween 80

0.7 g of HMT    1.4 g of HMT    1.9 g of HMT    2.4 g of HMT

FIGURE 19

| Sample | Triton X100 |
|---|---|
| Apparent density (g/cm$^3$)$^1$ | 0.148 |
| Skeletal density (g/cm$^3$)$^2$ | 1.456 |
| Porosity (%)$^3$ | 89.84 |
| Total pore volume (cm$^3$/g)$^3$ | 6.07 |
| Young's modulus (MPa) | 27.06 |
| Compression strength (MPa) | 1.24 |
| Thermal conductivity (W/m/K) | 0.0626 |
| Total intrusion volume (cm$^3$/g)$^4$ | 2.94 |
| Specific surface area (m$^2$/g)$^4$ | 17.50 |
| Median diameter of pores (μm)$^4$ | 0.38 |
| Average diameter of cells (μm)$^4$ | 0.67 |

[1] Determined by weighing cylindrical samples of known dimensions
[2] Determined by helium pycnometry
[3] Determined from measurements 1 and 2
[4] Determined by mercury porosimetry Figure 20
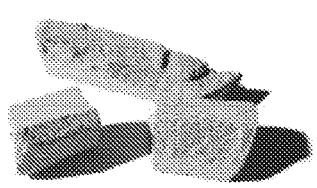 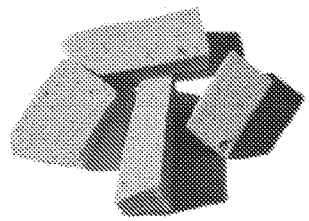 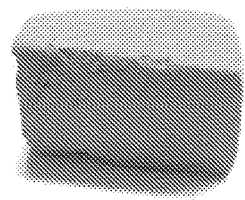
Triton X100　　　　　Tween 80　　　　　Cremophor ELP

FIGURE 21

| Sample | TFA2 | TFA2EG |
|---|---|---|
| Apparent density (g/cm$^3$)[1] | 0.127 | 0.127 |
| Skeletal density (g/cm$^3$)[2] | 1.433 | 1.413 |
| Porosity (%)[3] | 91.14 | 91.01 |
| Total pore volume (cm$^3$/g)[3] | 7.18 | 7.17 |
| Young's modulus (MPa) | 23.06 | 29.85 |
| Compression strength (MPa) | 1.58 | 1.59 |
| Thermal conductivity (W/m/K) | 0.0601 | 0.0655 |
| Total intrusion volume (cm$^3$/g)[4] | 3.82 | 4.02 |
| Specific surface area (m$^2$/g)[4] | 4.93 | 4.97 |
| Median diameter of pores (µm)[4] | 2.96 | 3.04 |
| Average diameter of cells (µm)[4] | 3.10 | 3.24 |

[1] Determined by weighing cylindrical samples of known dimensions
[2] Determined by helium pycnometry
[3] Determined from measurements 1 and 2
[4] Determined by mercury porosimetry

CELLULAR POROUS MONOLITHS CONTAINING CONDENSED TANNINS

BACKGROUND

The subject of the present invention is a process for the production of cellular porous monoliths of natural origin based on condensed tannins, the monoliths obtained by this process and applications thereof, as well as the emulsion and liquid foam enabling their manufacture.

"PolyHIPE" (Polymerized High Internal Phase Emulsion) materials, proposed for the first time in 1982 (EP 0060138), are obtained by polymerization of an emulsion termed HIPE (High Internal Phase Emulsion) composed on the one hand of an external or dispersant phase which is essentially constituted by polymerizable monomers and a surfactant agent in solution in a solvent, and on the other hand of an internal or dispersed phase which typically represents 74% or more of the total volume of the emulsion and which is essentially constituted by a solvent not miscible with the polymerizable monomers or with the solvent of the dispersant phase. After polymerization and removal of the solvent of the dispersed phase, open-cell materials are obtained the cells of which correspond to the imprint of the bubbles formed by that solvent in the course of the preparation of the emulsion and are interconnected by apertures of smaller size than themselves, commonly denoted by the term "pores". On account of their properties, polyHIPE materials are the subject of growing interest, and their utilization has been proposed in numerous fields, among which there may be mentioned the manufacture of disposable absorbent articles, articles for thermal, acoustic, electrical or mechanical insulation, membranes, filters or even supports for inks, colorants and catalysts.

Foams are complex materials constituted by the dispersion of a gas in a condensed medium. Depending on the type of condensed medium, foams can be liquid or solid.

The formation of foams is a process which is regularly observed in nature when in particular gases are mechanically mixed into a liquid.

Liquid foams are materials which are in everyday use: surfactant foams, shaving foam, foamed milk, cappuccino or beer.

Solid foams are more difficult to find in nature. In general, they are produced from the liberation of a gas in a high viscosity liquid which hardens while the gas is escaping.

Solid foams are a class of materials generally characterized by their lightness and their cellular structure which ensure solutions that are advantageous from the point of view of their application. They can be classified according to the type of cells. Open-cell foams have very interconnected cells, and as a result their structure is very permeable and light. Closed cell foams have much greater strength than the former because the walls are not perforated and can therefore withstand greater compressive stresses.

Another classification of the solid foams is based on their physical properties:

Elastic foams have the property of being deformable while resuming their original shape when the stress which is applied to them disappears. The market for these foams is dominated by the polyurethane foams but latexes and EVA foams are also much used in specific sectors such as mattresses and sports accessories.

In contrast, rigid foams are materials which do not deform and the main applications of which are in the thermal and acoustic insulation of buildings. Rigid foams are sometimes utilized as shock-proofing in automobiles for their ability to absorb stresses and mechanical energy, and for their lightness. The most widely sold rigid foams are polyurethanes and phenolics.

The vast majority of polyHIPE materials are obtained from polymers originating from petroleum resources which are not very environmentally friendly and the increasing scarcity of which entails a rise in production costs. Also, to decrease costs and for positioning as more environmentally friendly alternatives than these synthetic products derived from petrochemistry, and the production of which requires heavy energy expenditures, there has been a move towards "green" materials.

As regards the elastic foams, the commercial products mainly consist of polyurethanes, but some natural alternatives exist, in particular latexes, which are steadily increasing in the market. On the other hand, in the case of the rigid foams, practically no natural product is proposed as a replacement for the synthetic products.

"Green" materials, in particular those originating from biomass, should progressively replace their more expensive and less environmentally friendly synthetic equivalents. By biomass is meant all the lignocellulose products originating from agriculture and forestry (straw, fruit seeds and skins, wood and all other vegetable residues), but also derivatives thereof after separation by chemical, thermochemical or chemical-mechanical operations (lignin, cellulose, tannins, and all other furan and phenol compounds). The multifunctional nature of the materials originating from green chemistry allows an extraordinary variety of applications in the energy and environment fields.

Until now, few studies have been made and the only materials of the polyHIPE type manufactured from "green" material were produced from Kraft black liquor, a by-product of the paper-making industry (http://www.theses.fr/2011BOR14435). This liquor, heavily laden with various minerals, is difficult to utilize since the slightest variation in pH leads to the precipitation of the lignin. Moreover, the materials are extremely impure, which can be prejudicial for certain applications.

Therefore the inventors set themselves the problem of finding another material originating from biomass which would not have these disadvantages.

Well known for leather treatment, the tannins are polyphenolic components utilized by vegetables to defend themselves against insects and fungi. These substances are found in all vegetables in different percentages. The bark of trees in general contains the most significant quantity thereof, but tannin is present in the cytoplasm of all vegetable cells. The different woods store tannins in different areas of the vegetable: the pine (*Pinus radiata*), the oak (*Quercus robur*) and mimosa (*Acacia mearnsii* or *mollissima*) contain the majority of their tannins in the bark, and the gambier (*Uncaria Gambir*) in the leaves, whereas the chestnut (*Castanea sativa*) and the quebracho (*Schinopsis balansae*) store their tannins throughout their structure. The vegetable tannins can combine with proteins to give soluble or insoluble complexes. In spite of the differences in their compositions, they have a group of properties in common:

They precipitate proteins from their solution, in particular gelatin.

They give various colored lakes with the salts of heavy metals.

They precipitate with cationic colorants.

They are soluble in water to a greater or lesser extent and their solutions are always acidic.

They are amorphous and have no precise melting point.

In terms of chemical composition, the distinction is made between two families of tannins: hydrolyzable tannins and condensed tannins or flavonoids.

The hydrolyzable tannins are constituted by simple phenolic substances: these are esters of gallic acid and of dimers thereof (digallic acid, ellagic acid) and monosaccharides (above all glucose). The hydrolyzable tannins are often divided into gallotannins, resulting in gallic acid after hydrolysis, or ellagitannins releasing ellagic acid after hydrolysis. They have already been used as partial substitutes for phenol in the manufacture of phenol-formaldehyde resins; nonetheless their utilization remains very limited in the adhesives field on account of their low reactivity with formaldehyde. On the other hand, the chestnut and tara tannins are very much utilized in the tanning industry.

In contrast to the hydrolyzable tannins, the condensed tannins are not decomposable by hydrolysis. On the contrary, when subjected to heating in an acidic medium they progressively polymerize and form amorphous anthocyanin pigments, of red color, or insoluble yellow-brown products, of high molecular mass, called pholbaphenes. On pyrolysis, the condensed tannins yield pyrocatechol.

The condensed tannins are constituted by flavonoid units classified into four entities (Porter, L. J.: The flavonoids. J. B. Harborne, Ed., Chapman and Hall, London, 1988)

tannins of the prodelphinidine type having a ring A of the phloroglucinol type and a ring B of the pyrogallol type (the base component is gallocatechin, Figure A),

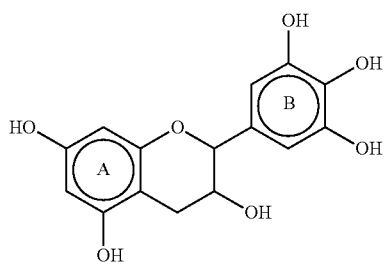

(A)

tannins of the procyanidine type having a ring A of the phloroglucinol type and a ring B of the catechol type (the base component is catechin, Figure B)

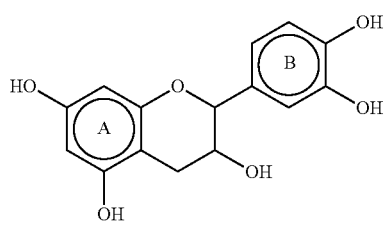

(B)

tannins of the type prorobinetinidine type having a ring A of the resorcinol type and a ring B of the pyrogallol type (the base component is robinetinidol, Figure C), and

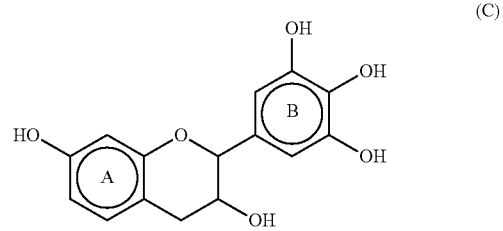

(C)

tannins of the profisetinidine type having a ring A of the resorcinol type and a ring B of the catechol type (the base component is fisetinidol, Figure D).

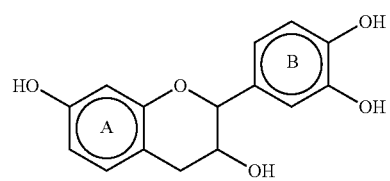

(D)

The units of condensed tannins are generally linked by 4-6 and 4-8 bonds. The condensed tannins have a repetition of 2 to 8 flavonoid units.

When mixed with water, a hardening agent and a foaming agent, the tannins produce extremely light rigid foams. Their remarkable properties, similar and even superior to the commercial phenolic foams currently utilized in aerospace and marine applications, combine mechanical strength, thermal insulation, non-flammability and infusibility.

When subjected to other conditions, the tannins polymerize to give rigid gels, which are elastic to a greater or lesser extent. At a density equivalent to that of the rigid foams, materials the porosity of which is 1,000 to 10,000 times narrower are obtained. These are then no longer referred to as thermal insulators but as potentially thermal "super insulators". The direct competitors of such ultra-light solids are the silica aerogels, very costly and originating from toxic chemistry. The aerogels from tannins are lighter, less expensive, non-irritant and opaque, which can make them still better in that they transmit very little or no infrared.

The pyrolysis of these two families of materials (foams and gels) leads to their equivalents in glassy carbon. The porous starting structure is retained, but the mechanical strength is improved with the heat treatment, at the same time as the resistance to thermal shock and chemical inertness.

Another valuable property became apparent: electrical conductivity. Not only are the uses of their organic precursors (sandwich composites, thermal and sound insulation, shock absorption, filtration of corrosive liquids or of molten metals) retained, but the carbon foams derived can also be utilized as porous electrodes, for electromagnetic shielding, heterogeneous catalysis, adsorption, etc. In addition, carbon aerosols from tannins have an excellent performance as supercapacitor electrodes. These devices, which serve for auxiliary electric power in trams, high-speed trains and other electric or hybrid vehicles, need further development and require properties of chemical inertness and porosity which the carbon gels are able to provide. About 5 times less expensive than their resorcinol-derived equivalents, the carbon aerogels from tannins are serious competitors for the storage of electrochemical energy.

The inventors have already described tannin-based foams prepared in a totally different manner, by physical and/or chemical foaming, that is to say the foam is formed by expansion and/or production of a gas in the formulation (Tondi G. et al. *Carbon* (2009), 47, No. 6, pages 1480-1492; *Bioresource Technology* (2009), 100, No. 21, pages 5162-5169; Zhao W. et al. *Materials Chemistry and Physics* (2010), 122, 175-182; Zhao W. et al. *Materials Chemistry and Physics* (2010), 123, 210-217; Basso M. C. et al. *Advanced Materials Letters* (2011), 2, 378-382; Ui X. et al. *Maderas Ciencia y Tecnologia* (2012), 14, 257-265; Li X. et al. *Carbon* (2012), 50, 2026-2036; Lacoste C. et al. *Industrial Crops and Products* (2013), 43, 245-250) and is not of the polyHIPE type.

It would therefore be desirable to have available a process for the preparation of materials which are either polyHIPEs, or foams, or hybrid products between polyHIPE and foams and which have high mechanical strength or, at the very least, sufficiently high for it to be possible genuinely to envisage their utilization in all the applications which have been proposed for this type of materials originating from petroleum resources and which makes use of the materials originating from biomass, which are inexpensive to produce.

SUMMARY

Also a first subject of the present invention is a process for the production of porous monolithic materials based on condensed tannins, said process comprising the following steps:
  a. obtaining a first liquid phase, said liquid phase being an aqueous solution of condensed tannins,
  b. obtaining a second phase, said second phase being either an oil or a volatile solvent not miscible with water, or air, or a mixture of oil and air or of a volatile solvent not miscible with water and air and said second phase not being miscible with the first phase, and at least one of said phases comprising a surfactant,
  c. dispersing said second phase in said first liquid phase, in the presence of a hardening agent,
  d. mixing said phases with stirring until the obtention:
    i. of a homogeneous and stable emulsion when the second phase is an oil or a volatile solvent not miscible with water, or
    ii. of a mixture which is macroscopically homogeneous but intermediate between an emulsion and a foam when the second phase is a mixture of oil and air or of a volatile solvent not miscible with water and air, or
    iii. of a foam when the second phase is air, and
  e. either,
    i. carrying out the polymerization of the emulsion or of the emulsion-foam intermediate obtained in step d.i) or in step d.ii) until the obtention of a solid, washing if necessary and drying said solid, or,
    ii. carrying out the polymerization and drying said foam obtained in step d.iii)

According to the invention, the washing step in e.i) is necessary only if oil or a mixture of oil and air is utilized as the second phase.

According to the invention, the surfactant can be present either in the aqueous liquid phase, or in the second phase when it contains oil or a volatile solvent not miscible with water, or in the aqueous liquid phase and in the second phase when it contains oil or a volatile solvent not miscible with water.

According to the invention, the oil can be of any origin, animal, vegetable or synthetic. It is advantageously of vegetable origin and advantageously selected from palm, soya, rape, sunflower, peanut, castor, linseed and olive oils. Sunflower oil is particularly valued. The quantity of oil has a direct effect on the porosity of the material since the size and number of the pores depend on the quantity of oil utilized. In the light of their knowledge and by routine tests, a person skilled in the art will know how to define the quantity of oil necessary for obtention of a material of desired porosity.

According to the invention, the volatile solvent can be any volatile solvent known to a person skilled in the art provided that it is not miscible with water (immiscible with water), for example cyclohexane or heptane. The term "volatile solvent not miscible with water" also covers mixtures of volatile solvents not miscible with water but miscible with one another.

In an advantageous embodiment of the process of the invention:
  A. either the first liquid phase is an aqueous phase of condensed tannin and the second phase a vegetable oil or a volatile solvent not miscible with water and, after hardening of the aqueous phase, extraction of the oil when the second phase is vegetable oil, then drying, a polyHIPE is obtained,
  B. or the first liquid phase is an aqueous phase of condensed tannin and the second phase air and, after hardening of the aqueous phase then drying, a rigid foam is obtained,
  C. or the first liquid phase is an aqueous phase of condensed tannin and the second phase a mixture of vegetable oil and air or of a volatile solvent not miscible with water and air and, after hardening of the aqueous phase, extraction of the oil when the second phase is vegetable oil, then drying, an aerated material "of the polyHIPE type" is obtained.

Thus, according to the invention, the oil extraction step in the embodiments A or C is necessary only if oil or a mixture of oil and air is utilized as the second phase. Said step is not necessary when a volatile solvent not miscible with water or a mixture of a volatile solvent not miscible with water and air is utilized.

In embodiment A, the porosity of the material is obtained by extraction of the vegetable oil from the hardened material or by simple evaporation of the volatile solvent not miscible with water from the hardened material. In embodiment B, the porosity of the material is obtained through the bubbles of air incorporated in the hardened material. In embodiment C, the porosity of the material is obtained both by extraction of the vegetable oil from the hardened material and by the incorporation of air or by the evaporation of the volatile solvent not miscible with water from the hardened material and by the incorporation of air; within the meaning of the present invention, by aerated material "of the polyHIPE type" is meant a material intermediate between a rigid foam and a polyHIPE.

In the embodiments A and B, the inventors have therefore developed an emulsion process, in particular of a vegetable oil-in-water emulsion or of an immiscible solvent in water emulsion which is however, depending on the proportions of the two phases present, capable of inverting between an aqueous solution of condensed tannin and a vegetable oil or between an aqueous solution of condensed tannin and a volatile solvent immiscible with water, and have shown for the first time that condensed tannins can be utilized directly in an emulsification process.

In an advantageous embodiment of the invention, when polyHIPEs are to be prepared, the first liquid phase can contain an antifoaming agent representing less than 1% by volume. This agent can be any antifoaming agent known to a person skilled in the art; it will advantageously be in liquid form. By way of example, polydimethylsiloxane may be mentioned. In the absence of antifoaming agent, the stirring speed must be controlled if aeration of the solution is to be avoided. In the presence of antifoaming agent, the stirring speed is no longer so important since there is no longer a risk of aeration of the solution. In all cases, the adaptation of these parameters is within the capabilities of a person skilled in the art. The speed will be selected in such a manner that the emulsion is not destabilized and will depend on the surfactant utilized. Advantageously the stirring speed, during the mixing of the two phases, will be comprised between 200 and 2000 rpm when a propeller mixer is used.

In another advantageous embodiment of the invention, the concentration of condensed tannin in the aqueous solution is comprised between 20 and 60% by mass of the total mass (condensed tannin+water), advantageously between 30 and 60% by mass and is advantageously equal to 40% by mass of the total mass (condensed tannin+water).

The pH of the solution of condensed tannin is typically of the order of 4.5; it can be adjusted to other values between 2 and 8 either by addition of an acid, advantageously para-toluenesulfonic acid, or by addition of a base, advantageously sodium hydroxide. Advantageously, the pH is comprised between 2 and 6.

In another advantageous embodiment of the process of the invention, when the first liquid phase is an aqueous phase of condensed tannin and the second phase a vegetable oil or a volatile solvent not miscible with water, the ratio oil/aqueous solution of condensed tannin or volatile solvent not miscible with water/aqueous solution of condensed tannin is comprised between 0.4/1 and 4/1 by volume.

In yet another advantageous embodiment of the process of the invention, when the first liquid phase is an aqueous phase of condensed tannin and the second phase is a mixture of vegetable oil and air or of volatile solvent not miscible with water and air, the ratio oil/aqueous solution of condensed tannin or volatile solvent not miscible with water/aqueous solution of condensed tannin is comprised between 0.3/1 and 4/1 by volume. The air/emulsion ratio can take any value up to 2/1 by volume, and advantageously be in ratio of 1/1 by volume. In other words, the total volume before polymerization is advantageously double that of the liquids (aqueous solution of condensed tannin and vegetable oil or volatile solvent not miscible with water) initially incorporated.

According to the invention, the condensed tannin can advantageously be selected from the group comprising tannins of the prodelphinidine type, procyanidine type, prorobinetinidine type, profisetinidine type, and any combination of said four types of tannin in any proportions. Advantageously said condensed tannin is selected from mimosa tannin, pine tannin and quebracho tannin.

According to the invention, any surfactant known to a person skilled in the art and selected from the group comprising non-ionic surfactants, and having a hydrophilic/lipophilic balance greater than 7, in particular greater than 10, can be used. Advantageously, ethoxylated castor oil or Polysorbate 80 is used.

The hardening agent is selected from those normally utilized in this type of process and can advantageously be selected from the group comprising aldehydes, oxazolidines, nitroparaffins, furfuryl alcohol and any combination of these hardening agents with each other in any proportions. As examples of aldehydes or of compounds capable of decomposing to aldehydes, hexamethylenetetramine (HMT), formaldehyde, paraformaldehyde, furfural, glutaraldehyde and glyoxal can be mentioned; as examples of nitroparaffins, trihydroxymethylnitromethane and homologous compounds can in particular be mentioned. The nature and the quantity of the hardening agent are connected to the nature of the condensed tannin utilized and a person skilled in the art will know, in the light of their general knowledge, how to select the type of hardening agent and the quantity. The hardening agent can be utilized in liquid form or in the form of a powder and a person skilled in the art will know how to select the most appropriate form. Hexamethylenetetramine will be utilized preferably as a powder.

The dispersion of the second phase in the first phase and the obtention of the emulsion can be carried out by any technique known to a person skilled in the art, for example by the process described in the thesis of Claire Forgacz (http://www.theses.fr/2011BOR14435).

In an advantageous embodiment of the invention, for the preparation of polyHIPEs or of polyHIPE-type material, the first liquid phase is an aqueous phase of condensed tannin and the second phase a vegetable oil or a mixture of vegetable oil and air and the process comprises the following steps:

a. preparing a solution of condensed tannin in water,
b. adjusting the pH of the solution obtained in step a) to a value comprised between 2 and 8,
c. stirring the solution obtained in the previous step at a speed comprised between 200 and 2000 rpm until the obtention of a homogeneous solution,
d. adding the surfactant and maintaining under stirring at a speed comprised between 200 and 2000 rpm until the obtention of a homogeneous solution,
e. incorporating the vegetable oil dropwise into the solution obtained in step d), while maintaining stirring of the mixture at a speed comprised between 200 and 2000 rpm until the obtention of a stable and homogeneous emulsion,
f. incorporating the hardening agent halfway through step e) and continuing stirring,
g. carrying out the polymerization at a temperature greater than ambient temperature, advantageously comprised between 40 and 90° C., still more advantageously equal to 85° C., until the obtention of a solid emulsion,
h. washing the solid obtained in the previous step with an organic solvent,
i. drying the polyHIPE or polyHIPE-type monolith.

The nature of the second phase vegetable oil alone or in a mixture of vegetable oil and air is determined by the severity of the stirring, for example via the speed of rotation of the propeller stirrer, and above all, in the case of the polyHIPEs, by the presence or otherwise of antifoaming agent. Thus, beyond typically 500 rpm, in the absence of antifoaming agent, air is mechanically incorporated in addition to the oil, and the bubbles are stabilized by the surfactant present. In this case, the total volume is greater than the sum of the two, and this is all the more so, the higher the speed and the longer it is maintained. Conversely, at low speed in the absence of antifoaming agent, typically in the region of 250 rpm, only the oil is incorporated, hence the total volume is equal to the tannin solution volume plus the oil volume.

According to the invention, the process described above can be carried out under the same conditions utilizing either a volatile solvent not miscible with water, or a mixture of volatile solvent not miscible with water and air as the second phase. In this case, the washing step h) is not necessary, the volatile solvent being removed by the drying step i).

In another advantageous embodiment of the process in which the first liquid phase is an aqueous phase of condensed tannin and the second phase a vegetable oil or a volatile solvent not miscible with water, the tannin solution used in step a) can comprise an antifoaming agent as previously defined and the surfactant be added not to the solution of condensed tannin but to the vegetable oil or to the volatile solvent not miscible with water.

The monolith obtained is rendered highly porous either by extraction of the oil when a solely oily second phase is utilized, or by evaporation when the second phase is a volatile solvent not miscible with water, or by extraction of the oil and incorporation of air when the second phase is a mixture of oil and air, or by evaporation of the solvent and incorporation of air when the second phase is a mixture of volatile solvent not miscible with water and air.

The organic solvent utilized in the washing step h) can be any solvent known to a person skilled in the art suitable for dissolving and extracting the oil. By way of example, methanol, ethanol and acetone can be mentioned. Ethanol, which is more compatible with the concept of green material, will be preferred.

The stirring speed is one of the parameters which makes it possible to control the pore size distribution and will be defined on the basis of the porosity desired. A person skilled in the art will know how to define the necessary speed in the light of their knowledge and by routine tests.

In a variant of the process according to the invention, it is possible to prepare the porous monolithic polyHIPE materials according to the following steps:
 a. preparing a mixture containing water, vegetable oil, a hardening agent, a surfactant and possibly an antifoaming agent,
 b. adjusting the pH of the mixture obtained in step a), to a value comprised between 2 and 8,
 c. stirring the mixture obtained in the previous step at a speed comprised between 200 and 2000 rpm until the obtention of a stable and homogeneous emulsion,
 d. adding the condensed tannin in powder form to the emulsion obtained in step c) and stirring at between 200 and 2000 rpm until the obtention of a new stable and homogeneous emulsion,
 e. carrying out the polymerization at a temperature greater than ambient temperature, advantageously comprised between 40 and 90° C., still more advantageously equal to 85° C., until the obtention of a solid emulsion,
 f. washing the solid obtained in the previous step with an organic solvent suitable for dissolving and extracting the oil,
 g. drying the monolith, which has been rendered highly porous.

As for the previous embodiment, it is the severity of the stirring, for example via the speed of rotation of the propeller stirrer, and the presence or otherwise of antifoaming agent, which defines the nature of the second phase.

In the latter embodiment, the oil utilized in step a) can be replaced by a volatile solvent not miscible with water. In this case, it will not be necessary to carry out the washing step f), the volatile solvent being removed by the drying step g).

In a variant of the process according to the invention, it is possible to prepare the porous monolithic materials of the polyHIPE type according to the following steps:
 a. preparing a mixture containing water, vegetable oil, a hardening agent, and a surfactant,
 b. adjusting the pH of the mixture obtained in step a), to a value comprised between 2 and 8,
 c. stirring the mixture obtained in the previous step at a speed comprised between 200 and 2000 rpm until the obtention of a stable and homogeneous emulsion,
 d. adding the condensed tannin in powder form to the emulsion obtained in step c) and stirring at between 200 and 2000 rpm until the obtention of a new stable and homogeneous emulsion,
 e. carrying out the polymerization at a temperature greater than ambient temperature, advantageously comprised between 40 and 90° C., still more advantageously equal to 85° C., until the obtention of a solid emulsion,
 f. washing the solid obtained in the previous step with an organic solvent suitable for dissolving and extracting the oil,
 g. drying the monolith, which has been rendered highly porous.

In this embodiment it is the severity of the stirring, for example via the speed of rotation of the propeller stirrer, which defines the nature of the second phase.

In all the variants of the process, following the mechanical stirring, either oil alone, or the solvent not miscible with water alone, or a mixture of oil and air, or a mixture of solvent not miscible with water and air, are incorporated into the solid emulsion, depending on the nature of the second phase which was utilized.

The mechanical stirring in the different steps can be carried out with any stirrer or any method available to a person skilled in the art, in particular blade stirrers or by the opposed pistons method.

The monolith obtained is rendered highly porous either by extraction of the oil when a solely oily second phase is utilized, or by extraction of the oil and incorporation of air when the second phase is a mixture of oil and air, or by evaporation of the solvent during drying when a volatile solvent not miscible with water is utilized, or by evaporation of the solvent during drying and incorporation of air when the second phase is a mixture of a volatile solvent not miscible with water and air.

The solvent utilized in the washing step f) can be any solvent known to a person skilled in the art suitable for dissolving and extracting the oil. By way of example, methanol, ethanol and acetone can be mentioned. Ethanol, which is more compatible with the concept of green material, will be preferred.

In another embodiment of the process of the invention, for the preparation of rigid foams, the first liquid phase is an aqueous phase of condensed tannin and the second phase air, and the process comprises the following steps:
 a. preparing a solution of condensed tannin in water,
 b. adjusting the pH of the solution obtained in step a), to a value comprised between 2 and 8,
 c. stirring the solution obtained in the previous step at a speed comprised between 400 and 600 rpm until the obtention of a homogeneous solution,
 d. adding the surfactant to the solution obtained in step c) and maintaining under stirring at a speed comprised between 200 and 2000 rpm until the obtention of a homogeneous liquid foam,
 e. incorporating the hardening agent halfway through step d) and continuing stirring,
 f. carrying out the polymerization at a temperature greater than ambient temperature, advantageously comprised between 40 and 90° C., still more advantageously equal to 85° C. for at least 24 hours,
g. drying the monolith.

In the different embodiments described above, step d), the preparation of the emulsion, can typically take several minutes to several tens of minutes, and advantageously 45 mins.

The materials obtained by the process of the invention are novel and are also part of the invention.

A further subject of the invention is also a porous monolithic polyHIPE material, of polyHIPE type or in the form of rigid foam, capable of being obtained by polymerization of condensed tannins by a process such as previously described.

The emulsion based on condensed tannins and the homogeneous liquid foam are novel and also form part of the invention.

Yet another subject of the invention is an emulsion, useful in particular for the preparation of a porous monolith material, comprising a first phase which is an aqueous solution of condensed tannins containing a hardening agent, and a second phase, based on oil, in particular vegetable oil, or a volatile solvent not miscible with water, or a mixture of oil and air, in particular of vegetable oil and air, or a mixture of volatile solvent not miscible with water and air, and at least one of said phases comprising a surfactant.

Yet another subject of the invention is a liquid foam, useful in particular for the preparation of a porous monolith material, comprising a first phase which is an aqueous solution of condensed tannins containing a surfactant and a hardening agent and a second phase which is air.

The polyHIPE and polyHIPE-type porous monolithic materials have an open and interconnected structure the apparent density of which is comprised between 0.03 and 0.5 g/cm$^3$.

The rigid foams have an apparent density which can reach 0.25 g/cm$^3$.

These materials are thermally insulating. They do not burn but are slowly consumed if a large amount of heat is applied. They are self-extinguishing.

They can be subjected to pyrolysis to give foams, polyHIPEs and polyHIPE-type materials in glassy carbon.

Thus another subject of the invention is a porous carbonized monolith capable of being obtained by pyrolysis of a porous monolithic material according to the invention.

The monoliths of the invention have the merit of having a simple chemical composition since they are constituted solely by organic material; they are therefore also functionalizable so as to be utilizable as catalyst supports.

Thus another subject of the invention is a functional porous organic monolith, in particular endowed with catalytic properties, capable of being obtained by functionalization of a porous monolithic material according to the invention.

They can be contacted either before pyrolysis with organic derivatives of silicon, or after pyrolysis with organic derivatives of silicon or liquid and/or gaseous silicon in order to be converted into silicon carbide foam of the same structure.

Thus a subject of the present invention is a porous monolith of silicon carbide (SiC) or Si—SiC composite capable of being obtained:
a. either by impregnation with preceramic polymers then pyrolysis of a porous monolithic material according to the invention,
b. or by liquid or gaseous silicon infiltration of a porous carbonized monolith according to the invention,
c. or by combination of the two methods.

The porous monolithic materials according to the invention can be utilized in the field of catalysis, chromatography, thermal or sound insulation, shock absorption, tissue engineering and drug release. The solid foams can also be utilized as floral foams.

BRIEF DESCRIPTION OF THE DRAWINGS

The invention is illustrated by the following Examples 1 to 9 and FIGS. 1 to 22.

In the following figures, the total intrusion volume of the monoliths and the specific surface area of the monoliths are measured by mercury intrusion up to a pressure of 4 MPa. The median diameter of the pores of the monoliths is determined by mercury intrusion as the pore diameter at which 50% of the total porous volume is filled by the mercury and the average diameter of the cells of the monoliths is determined from electron micrographs.

FIG. 1 summarizes the properties of polyHIPE monoliths prepared from a solution of mimosa tannin at pH 2.5 and variable concentrations of sunflower oil according to Example 1. F45A: 45 ml of sunflower oil/40 ml of 40% by mass solution of mimosa tannin with respect to the total mass (water+mimosa tannin); F75A: 75 ml of sunflower oil/40 ml of 40% by mass solution of mimosa tannin with respect to the total mass (water+mimosa tannin); F105A: 105 ml of sunflower oil/40 ml of 40% by mass solution of mimosa tannin with respect to the total mass (water+mimosa tannin).

FIG. 2 shows scanning electron micrographs, at 2 different magnifications, of the monoliths described in FIG. 1.

FIG. 3 summarizes the properties of polyHIPE monoliths prepared from a solution of mimosa tannin at pH 6 and variable concentrations of sunflower oil according to Example 1. F45B: 45 ml of sunflower oil/40 ml of 40% by mass solution of mimosa tannin with respect to the total mass (water+mimosa tannin); F75B: 75 ml of sunflower oil/40 ml of 40% by mass solution of mimosa tannin with respect to the total mass (water+mimosa tannin); F105B: 105 ml of sunflower oil/40 ml of 40% by mass solution of mimosa tannin with respect to the total mass (water+mimosa tannin).

FIG. 4 summarizes the properties of polyHIPE-type aerated monoliths prepared from a solution of mimosa tannin at pH 4 and variable concentrations of sunflower oil according to Example 2. F30-4-2k: 30 ml of sunflower oil/40 ml of 40% by mass solution of mimosa tannin with respect to the total mass (water+mimosa tannin); F60-4-2k: 60 ml of sunflower oil/40 ml of 40% by mass solution of mimosa tannin with respect to the total mass (water+mimosa tannin); F90-4-2k: 90 ml of sunflower oil/40 ml of 40% by mass solution of mimosa tannin with respect to the total mass (water+mimosa tannin).

FIG. 5 shows scanning electron micrographs, at 2 different magnifications, of the monoliths described in FIG. 4.

FIG. 6 summarizes the properties of polyHIPE-type aerated monoliths prepared from a solution of mimosa tannin at pH 6 and variable concentrations of sunflower oil according to Example 2. F30-6-2k: 30 ml of sunflower oil/40 ml of 40% by mass solution of mimosa tannin with respect to the total mass (water+mimosa tannin); F60-6-2k: 60 ml of sunflower oil/40 ml of 40% by mass solution of mimosa tannin with respect to the total mass (water+mimosa tannin);

F90-6-2k: 90 ml of sunflower oil/40 ml of 40% by mass solution of mimosa tannin with respect to the total mass (water+mimosa tannin).

FIG. 7 summarizes the properties of polyHIPE-type aerated monoliths prepared from a solution of mimosa tannin at pH 8 and variable concentrations of sunflower oil according to Example 2. F30-8-2k: 30 ml of sunflower oil/40 ml of 40% by mass solution of mimosa tannin with respect to the total mass (water+mimosa tannin); F60-8-2k: 60 ml of sunflower oil/40 ml of 40% by mass solution of mimosa tannin with respect to the total mass (water+mimosa tannin); F90-8-2k: 90 ml of sunflower oil/40 ml of 40% by mass solution of mimosa tannin with respect to the total mass (water+mimosa tannin).

FIG. 8 summarizes the properties of foam type monoliths prepared from a solution of mimosa tannin at pH 2.8 and at variable concentrations according to Example 3. F20-40: 30 ml of 20% by mass solution of mimosa tannin with respect to the total mass (water+mimosa tannin); F40-40: 30 ml of 40% by mass solution of mimosa tannin with respect to the total mass (water+mimosa tannin); F50-40: 30 ml of 50% by mass solution of mimosa tannin with respect to the total mass (water+mimosa tannin).

FIG. 9 shows scanning electron micrographs of the monoliths described in FIG. 8.

FIG. 10 summarizes the properties of the porous carbonized monoliths CF45A, CF75A and CF105A prepared according to Example 4, from F45A, F75A and F105A of Example 1 respectively.

Figure 11A:
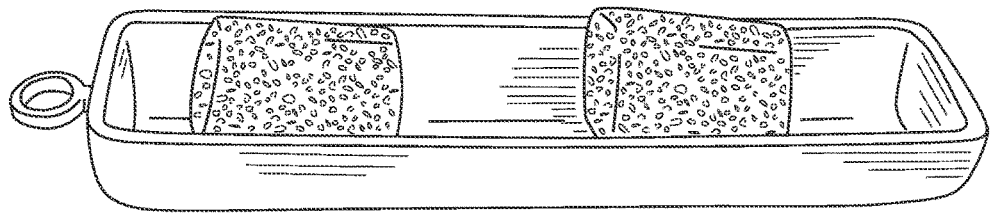
Figure 11B:
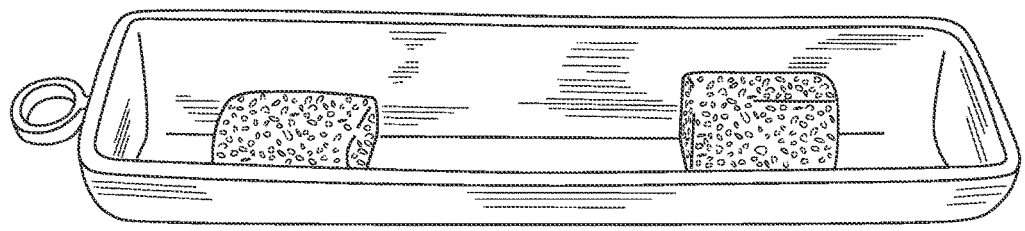

FIG. 11A shows the porous monoliths before carbonization (on the left F60-4-2k and on the right F30-4-2k) and FIG. 11B, the corresponding porous carbonized monoliths (on the left CF60-4-2k and on the right CF30-4-2k), obtained according to Example 4 from F60-4-2k and F30-4-2k of Example 2.

FIG. 12 summarizes the properties of the porous carbonized monoliths CF30-6-2k, CF60-6-2k and CF90-6-2k prepared according to Example 4, from F30-6-2k, F60-6-2k and F90-6-2k of Example 2 respectively.

Figure 13:
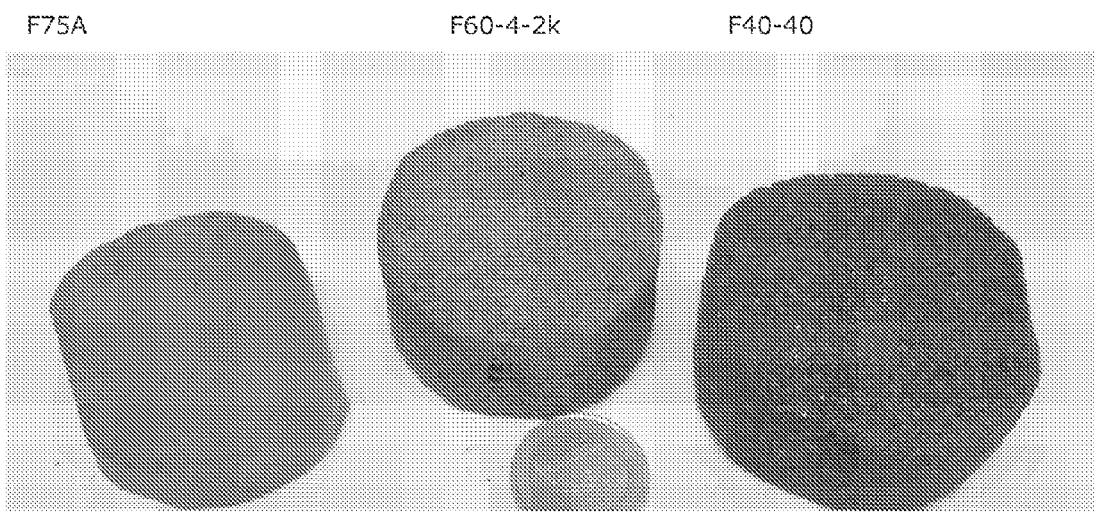

FIG. 13 shows the three types of organic materials originating from mimosa tannin (hence not carbonized) obtained according to the processes of the invention: on the left porous polyHIPE monolith, F75A, obtained according to Example 1, from an emulsion of an aqueous solution of mimosa tannin with sunflower oil (porosity about 88%), in the center porous polyHIPE-type monolith polyHIPE, F60-4-2k, obtained according to Example 2, from an emulsion based on an aqueous solution of mimosa tannin and sunflower oil, into which air has been mechanically incorporated (porosity about 94%), and on the right porous foam-type monolith, F40-40, obtained according to Example 3 from a liquid foam formed from an aqueous solution of mimosa tannin and air (porosity about 97%).

FIG. 14 summarizes the properties of the cellular polyHIPE monoliths prepared according to Example 5. TC monolith prepared with cyclohexane as the second liquid phase; TH monolith prepared with sunflower oil as the second liquid phase.

FIG. 15 shows the three types of cellular polyHIPE monoliths prepared according to Example 5. Cyclohexane: monolith prepared with cyclohexane as the second liquid phase; Heptane: monolith prepared with heptane as the second liquid phase; Sunflower oil: monolith prepared with sunflower oil as the second liquid phase.

FIG. 16 summarizes the properties of the foam-type monoliths prepared according to Example 6 utilizing Tween 80 as the surfactant.

FIG. 17 shows two types of foam-type monoliths prepared according to Example 6. Pluronic 6800: foam prepared with Pluronic 6800 as the surfactant and Tween 80: foam prepared with Tween 80 as the surfactant.

Figure 18:
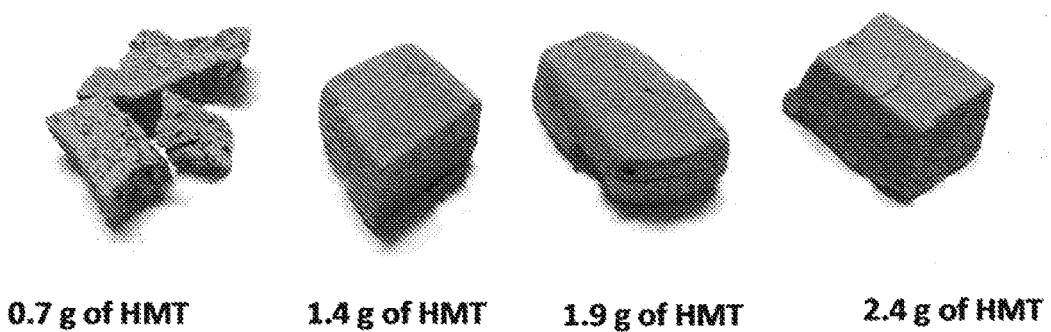

FIG. 18 shows five types of cellular polyHIPE monolith prepared according to Example 7 obtained from formulations containing different concentrations of hardening agent.

FIG. 19 summarizes the properties of the cellular polyHIPE monoliths prepared according to Example 8 utilizing Triton X 100 as the surfactant.

FIG. 20 shows three types of cellular polyHIPE monoliths prepared according to Example 8 obtained from formulations containing different types of surfactants: Tween 80, Triton X100 and Cremophor ELP.

FIG. 21 summarizes the properties of the cellular polyHIPE monoliths prepared according to Example 9; TFA2: surfactant Cremophor ELP 2% with respect to the total mass of the solution and TFA2G: influence of ethylene glycol at a concentration of 5% with respect to the total mass of the solution.

Figure 22:
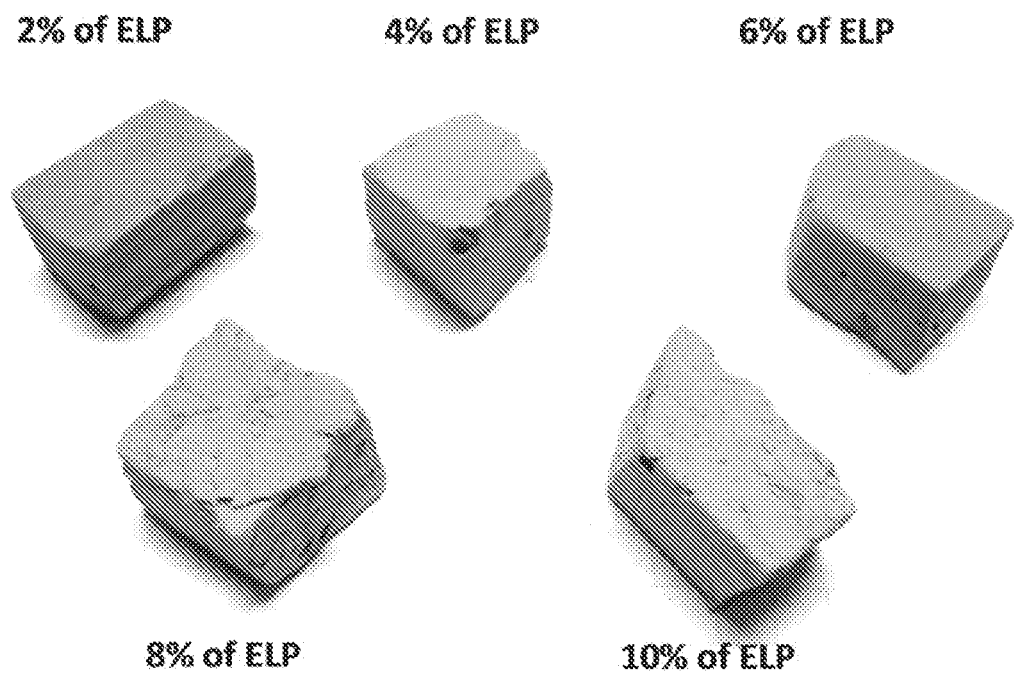

FIG. 22 shows five types of cellular polyHIPE monoliths prepared according to Example 9 obtained from formulations containing furfuryl alcohol as the hardening agent and different quantities of surfactant (2, 4, 6, 8 and 10% of Cremophor ELP with respect to the total mass of the solution).

DETAILED DESCRIPTION

Example 1: Porous polyHIPE Monoliths Prepared from Emulsion: Sunflower Oil/Water, without Air 1.1. Procedure Reagents utilized:
  commercial mimosa tannin utilized as is
  water
  hardening agent: 30% by mass aqueous solution of hexamethylenetetramine (hexamine)
  Surfactant: Cremophor® ELP (ethoxylated castor oil)
  Sunflower oil
  2M sodium hydroxide or para-toluenesulfonic acid (PTSA) in powder form Monoliths are prepared from the following emulsions:

| Emulsion | | F45A | F75A reference solution | F105A |
|---|---|---|---|---|
| Tannin solution | Tannin (g) | 20 | 20 | 20 |
| | Water (g) | 30 | 30 | 30 |
| | Tannin/(water + tannin) (%) | 40 | 40 | 40 |
| | Surfactant (g) | 1.33 | 1.33 | 1.33 |
| | Surfactant/(water + tannin) (%) | 2.6 | 2.6 | 2.6 |
| pH of tannin solution | | 2.5 | 2.5 | 2.5 |
| Tannin/oil (mL/mL) | | 40/45 | 40/75 | 40/105 |
| Speed of rotation (rpm) | | 250 | 250 | 250 |

The different steps are as follows:

1$^{st}$ Step—Preparation of the Solution of Mimosa Tannin

A solution of mimosa tannin is prepared by adding the mimosa tannin to water. The pH of the solution is adjusted with 2M sodium hydroxide or para-toluenesulfonic acid (PTSA). The mixture is mechanically stirred at 250 rpm for 10 minutes with a propeller stirrer equipped with a 3-blade propeller in order to obtain a very homogeneous solution.

2$^{nd}$ Step—Addition of the Surfactant

The surfactant is added to the solution of mimosa tannin obtained in the previous step and the mixture stirred at 250 rpm for 20 minutes; a homogeneous brown solution is obtained.

3$^{rd}$ Step—Addition of the Sunflower Oil

The sunflower oil is added dropwise, with stirring at 250 rpm, at the rate of 44 drops/min. While the oil is being added, 4.47 g of the hexamine solution is also added to the mixture. During the addition of the hexamine, the stirring speed is temporarily increased to 900 rpm for about 30 secs in order to facilitate the dissolution of the hexamine, then returned to 250 rpm.

4$^{th}$ Step—Heating of the Mixture

The vessel containing the mixture obtained in the previous step is covered with a plastic film or an aluminum film in order to avoid the emulsion drying on the surface, and placed in a ventilated oven at 85° C. for 20 hours. The gelling is very rapid, about 15 minutes for all the formulations. However, 20 hours at 85° C. are necessary to have complete crosslinking reactions and obtain totally hardened monoliths.

5$^{th}$ Step—Washing of the Samples in Acetone

After heating for 20 hours, the hardened monoliths are removed from the oven and allowed to cool to ambient temperature. The monoliths are next cut into cylindrical shape, placed in a Soxhlet extractor then washed with hot acetone under reflux for 7 days.

6$^{th}$ Step—Drying of the Samples

After washing for 7 days, the samples are dried at ambient temperature for 7 days.

7$^{th}$ Step—Measurement of Physical Properties of the Samples

These properties are measured by techniques known to a person skilled in the art.

and on the other by the change in emulsion type: from "oil-in-water" to "water-in-oil" when the volume fraction of oil increases, the inversion of the emulsion is observed when the images of the materials F45A and F105A are compared. F45A shows the cellular structure typical of a polyHIPE, i.e. displays a continuous solid phase having rather spherical cells, connected to one another by rather circular apertures. The strands, of triangular cross-section, are solid. The porous structure is thus hierarchical: cellular on the macroscopic scale, with much narrower and very numerous interconnections in the walls of the cells. F105 also has a cellular structure, but based on a stack of hollow spheres in which apertures are opened. The strands, of triangular cross-section, are hollow. F75A also shows this type of structure, the average diameters of the cells and the connections (the "pores") vary in a complex manner with the total porosity, in conjunction with the changes in structure observed by electron microscopy. These changes are explained by: (i) the inversion of the emulsion beyond a critical quantity of sunflower oil; (ii) the competition between porosity created by the sunflower oil and lost due to shrinkage in the course of the process; (iii) the fact that the level of surfactant remained constant in these Example, in spite of very different fractions of sunflower oil in the emulsion, consequently, for the single examples given here, the mechanical properties do not display a regular trend. They are remarkably high, considering the corresponding total porosity values.

Example 2: Porous Aerated polyHIPE-Type Monoliths Prepared from Emulsion: Sunflower Oil and Air/Water 2.1 Procedure Monoliths are prepared from the following emulsions:

|  |  | Emulsion | | | | | | | | |
|---|---|---|---|---|---|---|---|---|---|---|
|  |  | F30-4-2k | F30-6-2k | F30-8-2k | F60-4-2k | F60-6-2k | F60-8-2k | F90-4-2k | F90-6-2k | F90-8-2k |
| Tannin solution | Tannin (g) |  | 30 |  |  | 30 |  |  | 30 |  |
|  | Water (g) |  | 20 |  |  | 20 |  |  | 20 |  |
|  | Tannin/(water + tannin) (%) |  | 15 |  |  | 15 |  |  | 15 |  |
|  | Surfactant (g) |  | 2.33 |  |  | 2.33 |  |  | 2.33 |  |
|  | Surfactant/(water + tannin) (%) |  | 4.6 |  |  | 4.6 |  |  | 4.6 |  |
| ph of tannin solution |  | 4 | 6 | 8 | 4 | 6 | 8 | 4 | 6 | 8 |
| Tannin/oil (mL/mL) |  |  | 40/30 |  |  | 40/60 |  |  | 40/90 |  |
| Speed of rotation (rpm) |  |  | 2000 |  |  | 2000 |  |  | 2000 |  |

1.2. Results

These are given in the tables in FIGS. 1 and 3 and in FIG. 2 for monoliths prepared from a solution of mimosa tannin with 20 g of mimosa tannin in 30 g water. On the basis of FIGS. 1 to 3, it can be observed that:

the porosity of the monoliths is very high, of the order of 90%, which is remarkable for this type of material, the porosity increases with the fraction of sunflower oil incorporated in the emulsion, but without proportionality. This is a common property of the polyHIPEs which is explained on the one hand by the shrinkage of the materials during the hardening and drying phases, The different steps are as follows:

20 g of water, 30, 40 or 60 mL of sunflower oil, 4.47 g of the aqueous solution of hexamine, 1.3 g of surfactant and sodium hydroxide (quantity necessary to have a pH of 4, 6 or 8) are mixed at 2000 rpm until a white, stable and homogeneous emulsion is obtained. 30 g of mimosa tannin is added and the mixture is stirred for 45 minutes at 2000 rpm.

The hardening, washing and drying are carried out under the same conditions as for steps 4 to 6 of Example 1.

2.2 Results

These are given in the tables in FIGS. 4, 6 and 7, and in FIG. 5. Because of the air incorporated during preparation, a dome appears on the surface of the samples, a dome which does not appear in the monoliths prepared according to Example 1. On the basis of FIGS. 4 to 7, it can be observed that:

- as could have been expected, the porosity is higher (i.e. the apparent density is much lower) than that of the corresponding polyHIPEs prepared with comparable mimosa tannin/sunflower oil proportions. This is explained by the presence of air incorporated into the structure during the mechanical stirring,
- this air makes it possible to obtain porous monolithic materials of different structure from that of the previous polyHIPEs at constant proportions of sunflower oil/aqueous solution of mimosa tannin. Conversely, structures qualitatively similar (cellular) to the previous polyHIPEs can be observed for different initial compositions. However, the cells then have much greater average diameters in the presence of air (compare the series F45A-F105A with the series F30-4-2K-F90-4-2K using the same magnification: that for which the scale bar is 1 mm),
- consequently, the incorporation of air via more or less vigorous stirring of the phases present makes it possible to vary the average diameter of the cells considerably, which is not enabled by the variation of only one of the parameters of the formulation at a time,
- the porosity decreases when the proportion of oil in the emulsion increases. This result, unexpected a priori but well verified in all cases, shows that air is much easier to incorporate into an emulsion less rich in sunflower oil, and that it then more easily contributes to the creation of porosity than does the sunflower oil,
- the mechanical properties remain high considering the porosity present, and increase steadily as the porosity decreases. This result is to be expected since the porous structure does not change when the porosity varies,
- consequently, the pores are consistently wider when the porosity increases. This trend is seen more clearly from the mercury porosimetry results than on the micrographs.

Example 3: Porous Monoliths Prepared from Foams 3.1. Procedure

Monoliths are prepared as follows. An aqueous solution of mimosa tannin the concentration of which is 20, 40 or 50% of the total mass (mimosa tannin+water) is prepared by mixing 7.5, 20 or 30 g of mimosa tannin, respectively, with 30 g of water. This solution is then mixed with PTSA, in sufficient quantity to reach pH 2.8, for 10 minutes at 500 rpm. At the end of this period, the surfactant is added and all the ingredients are mixed at 2000 rpm until the obtention of a homogeneous foam, without any condensed liquid phase remaining, namely 40 mins. After half the time, 4.7 g of 30% hexamine solution is added. The foam obtained is covered with a film and placed in a ventilated oven at 85° C. for 24 hrs. Next the samples are cut up and placed in a room at ambient temperature to dry in air for several days or in the same ventilated oven for a few hours. The table below summarizes the ingredients and the preparation conditions.

|  | Liquid foam | F20-40 | F40-40 | F50-40 |
|---|---|---|---|---|
| Tannin solution | Tannin (g) | 7.5 | 20 | 30 |
|  | Water (g) | 30 | 30 | 30 |
|  | tannin/(water + tannin) (%) | 20 | 40 | 50 |
|  | PTSA (g) | 1.12 | 1.12 | 1.12 |
|  | Surfactant (g) | 2.25 | 3 | 3.6 |
|  | Surfactant/(water + tannin) (%) | 6 | 6 | 6 |
| pH of the tannin solution | | 2.8 | 2.8 | 2.8 |
| Stirring time (mins) | | 40 | 40 | 40 |
| Speed of rotation (rpm) | | 2000 | 2000 | 2000 |

3.2. Results

These are given in the table in FIG. 8, and in FIG. 9. On the basis of FIGS. 8 and 9, it can be observed that:

- the porous structure is rather different from that of the materials of the previous Examples 1 and 2. The structure is in fact that of a crosslinked foam, the materials obtained according to the variants of the process according to Examples 1 or 2 being more cellular,
- thus, the connections between cells are not as multiple as previously, since they essentially correspond to the walls of the cells which existed in the liquid foam. From that structure, the solid foam has only retained the intersections of the bubble walls, in other words the strands. This is further confirmed by the specific surface area, much lower for the foams than for the other monoliths of equivalent porosity,
- the density differences become apparent in these foams by considerable changes both in the thickness of the solid phase (the strands) and the diameter of the empty spaces,
- it is much easier by this method (without oil) to obtain very wide porosity (the scale bar here is 2 mm as against 1 mm in the previous photos) and hence greater porosity,
- the porosity is readily modifiable by changing the concentration of the tannin solution, as illustrated, or by changing the nature of the surfactant,
- at comparable total porosity, the mechanical properties of the foams are inferior to those of the polyHIPE or polyHIPE-type monoliths. As suggested above, this is explained by the different pore structure, which is much more open in the case of the foams.

Example 4: Preparation of Porous Carbonized Monoliths 4.1. Procedure

The monoliths obtained with the emulsions F45A, F75A and F105A of Example 1 and the monoliths obtained with the emulsions F30-6-2k, F60-6-2k and F90-6-2k of Example 2 are utilized The carbonization of the samples is carried out in a horizontal tubular furnace at 900° C. for 2 hrs under a nitrogen atmosphere (5° C./min-50 mL/min).

4.2. Results

These are given in the tables in FIGS. 10 and 12 and in FIG. 11. On the basis of FIGS. 10 to 12, it can be observed that

- the samples withstand the heat treatment very well, and the porous carbons obtained have a structure identical to that of the original monoliths. They are free from cracks, the variation in the porosity follows exactly the same trends as those for the precursor organic materials, within experimental error (in particular at very high porosities, >95%), the porosity of the carbonized materials is greater than that of the organic precursors, the pyrolysis having resulted in a loss in mass and a comparable shrinkage in size (about 60%), the apparent density of the carbonized materials changes little with respect to that of the organic precursors, within individual variations in samples (a large number of samples is necessary to observe it, on account of the experimental scatter of the data), owing to the shrinkage, the pores and the cells are always smaller in the carbonized materials, the loss of gas which accompanies the pyrolysis produces very fine pores which have the effect that the specific surface area of the carbonized materials is always greater than that of their organic equivalents, the mechanical properties are considerably increased after pyrolysis.

Example 5: Process for the Preparation of Cellular polyHIPE Monoliths Utilizing a Volatile Solvent not Miscible with Water as the Second Liquid Phase and a Hardening Agent in Powder Form Rather than in Solution 5.1. Procedure a. 20 g of mimosa tannin, 1.9 g of hexamethylenetetramine (HMT) powder and 6 drops of antifoaming agent (polydimethylsiloxane) are dissolved in 33.9 g of distilled water, then 0.7 g of solid para-toluenesulfonic acid (PTSA) are added to adjust the pH of the solution to 2.5. The mass fraction of the solids with respect to water is thus 40%. The mixture is stirred for 10 minutes with a paddle stirrer rotating at 500 rpm in order to obtain a very homogeneous solution.

b. 2.97 g of surfactant is added to the solution obtained in step a) (Cremophor ELP=5% with respect to the total mass of said solution) and the mixture is stirred for 10 minutes with a paddle stirrer rotating at 500 rpm in order to obtain a very homogeneous solution (and without bubbles, owing to the presence of antifoaming agent).

c. The speed of rotation of the stirrer blades is increased to 1000 rpm and 150 mL of the second liquid phase (not miscible with the first), cyclohexane or heptane, are incorporated very gradually (usually 44 drops/minute).

d. The emulsion obtained is poured into a container that closes hermetically in order to avoid evaporation of the volatile solvents utilized and placed in an oven at 70° C. for 24 hrs. Gelling takes place in 40-45 minutes, and good hardening of the material and better mechanical properties after drying are obtained after 24 hrs.

e. When the second liquid phase is cyclohexane or heptane, no washing in a Soxhlet is necessary to develop the porosity, contrary to the case with oil. In the presence of cyclohexane or heptane, a simple drying in air for 3-4 days is sufficient to obtain a dry and highly porous polyHIPE.

After drying in air for 3-4 days, a dry and highly porous polyHIPE is obtained.

A cellular polyHIPE monolith is prepared in the same manner with sunflower oil as the second liquid phase.

The preparation conditions are summarized in the table below for two materials prepared under strictly identical conditions according to the protocol described above, with the only difference that the first (TC) was prepared with cyclohexane as the second liquid phase, and the second (TH) for comparison with sunflower oil as the second liquid phase.

| Sample | TC | TH |
|---|---|---|
| Mass fraction of solids (%) | 40 | 40 |
| Mass fraction of surfactant (%) | 5 | 5 |
| Volume fraction of second phase (%) | 75 | 75 |
| Initial pH | 2.5 | 2.5 |
| Speed of rotation in step b) | 500 | 500 |
| Speed of rotation in step c) | 1000 | 1000 |

5.2. Results

These are given in FIGS. 14 and 15.

The properties of the two materials (TC) and (TH) thus prepared are given in the table in FIG. 14 and in FIG. 15.

The materials prepared with the volatile solvent instead of the oily phase are shorter in length and thus simpler to prepare, and have a porosity which is both more developed and narrower. These are excellent thermal insulators. The mechanical properties are not appreciably different from those of their equivalents prepared with oil.

With heptane as the second phase, a material with very similar properties is obtained (FIG. 15).

Example 6: Process for the Preparation of Foam Type Cellular Monoliths Utilizing Air and Different Types of Surfactants as the Second Phase 6.1. Procedure The preparation is carried out according to the method described in Example 3 with a tannin/(water+tannin) ratio=40% by mass. The only difference comes from the utilization of hexamethylenetetramine (or hexamine or HMT) in powder form rather than in solution.

Different surfactants are utilized: Tween 80 (polyoxyethylene (20) sorbitan monooleate), Pluronic P-123 (poly(ethylene glycol)-block-poly(propylene glycol)-block-poly(ethylene glycol)) and Pluronic 6800 (ethylene glycol propylene glycol adipate).

The conditions for the preparation of the formulation utilizing Tween 80 are given below:

| Tannin solution | Tannin (g) | 20 |
|---|---|---|
| | Water (g) | 30 |
| | tannin/(water + tannin) (%) | 40 |
| | PTSA (g) | 1.12 |
| | Surfactant (g) | 3 |
| | Surfactant/(water + tannin) (%) | 6 |
| Initial pH of tannin solution | | 2.8 |
| Stirring time (mins) | | 40 |
| Speed of rotation (rpm) | | 2000 |

For the other formulations, the preparation conditions are identical.

6.2. Results

These are given in FIGS. 16 and 17.

The properties of the material obtained from the formulation utilizing Tween 80 are directly comparable to those of the material F40-40 of Example 3 illustrated in FIG. 8, which was prepared from a formulation in which the surfactant is Cremophor ELP (FIG. 16). Compared to that prepared with Cremophor ELP, the material obtained from the formulation utilizing Tween 80 appears more homogenous and visibly shows cells of smaller sizes. This feature explains the fact that at equivalent porosity the material prepared with Tween 80 has much better mechanical properties than those of the sample F40-40.

The material obtained from the formulation utilizing Pluronic 6800 likewise shows very good macroscopic properties (FIG. 17).

Example 7: Process for the Preparation of Cellular polyHIPE Monoliths, Utilizing Vegetable Oil as the Second Phase, and Different Quantities of Hardening Agent in Powder Form 7.1 Procedure The purpose being to examine the effect of the quantity of hardening agent (hexamethylenetetramine: HMT) on the properties of the final products, the preparation protocol is identical to that of Example 5 apart from the following exceptions:
the quantities of water and surfactant are slightly modified so as to maintain the mass fractions of solids and surfactant constant at 40% and 5% respectively;
there is no antifoaming agent added and for that reason the stirring speed of the stirrer blades is limited to 250 rpm during the whole process.

The formulations utilizing different quantities of HMT are therefore as follows:

| Name of material | TH07 | TH14 | TH19 | TH24 | TH29 |
|---|---|---|---|---|---|
| Tannin (g) | 20 | 20 | 20 | 20 | 20 |
| Water (g) | 32.1 | 33.17 | 33.9 | 34.65 | 35.4 |
| PTSA (g) | 0.7 | 0.7 | 0.7 | 0.7 | 0.7 |
| HMT (g) | 0.7 | 1.4 | 1.9 | 2.4 | 2.9 |
| Cremophor ELP (g) | 2.82 | 2.9 | 2.97 | 3.04 | 3.11 |
| Sunflower oil (mL) | 150 | 150 | 150 | 150 | 150 |

7.2 Results

These are given in FIG. 18.

The sample TH19 is that which displays the most homogenous structure and the best macroscopic properties.

The sample TH07 is multiply fissured and its pore structure is completely disordered and poorly defined.

The material TH29 could not be prepared as it is impossible to obtain the initial emulsion because of hardening that is much too rapid.

The samples TH14 and TH24 are rather similar, but less homogeneous than TH19, which is thus the best compromise.

Example 8: Process for the Preparation of Cellular polyHIPE Monoliths, Utilizing Vegetable Oil as the Second Phase and Different Types of Surfactant 8.1. Procedure The purpose being to examine the effect of the nature of the surfactant on the properties of the final products, the preparation protocol is identical to that of Example 5, apart from the following exceptions:
the quantity of surfactant introduced in step b) is 1.8 g;
in step c), the stirring speed is 1500 rpm and the quantity of sunflower oil is 80 mL.

The following different surfactants were then tested: Pluronic 7400 (BASF), Triton X100 (Prolabo), Pluronic 6800 (BASF), TWEEN 80 (Sigma Aldrich), Pluronic 123 (Sigma Aldrich), Pluronic 127 (Sigma Aldrich) and Cremophor ELP (Sigma Aldrich).

The conditions for the preparation of the different formulations are given in the table below:

| Sample | Surfactant |
|---|---|
| Mass fraction of solids (%) | 40 |
| Mass fraction of surfactant (%) | 3 |
| Volume fraction of second phase (%) | 67 |
| Initial pH | 2.5 |
| Speed of rotation in step b) | 500 |
| Speed of rotation in step c) | 1500 |

8.2. Results

These are given in FIGS. 19 and 20.

The following observations can be made:
i. Pluronic 7400 (BASF): good emulsion, of very suitable viscosity, difficult to use at low stirring speed (hence need to stir at 1500 rpm), possible polyHIPE.
ii. Triton X100 (Prolabo): excellent emulsion even at low stirring speed, excellent final polyHIPE.
iii. Pluronic 6800 (BASF): good emulsion provided that stirring is fast enough, good final polyHIPE.
iv. TWEEN 80 (Sigma Aldrich): emulsion of lower viscosity than with Cremophor ELP, but of good quality and homogeneous even at low stirring speed, excellent final polyHIPE.
v. Pluronic 123 (Sigma Aldrich): fine emulsion, easy to mix, good final polyHIPE.
vi. Pluronic 127 (Sigma Aldrich): fine emulsion but only after mixing at high speed, long and difficult as Pluronic 127 is of low solubility, good final polyHIPE.
vii. Cremophor ELP (Sigma Aldrich): perfect under almost all conditions.

Compared to its equivalent prepared with Cremophor ELP, the material which was prepared on the basis of Triton X100 is more porous, and the porosity is constituted by finer pores. This results in mechanical properties superior to those of the material prepared with Cremophor ELP under the same conditions.

The material obtained from the formulation utilizing Tween 80 likewise shows good macroscopic properties (FIG. 20).

Example 9: Process for the Preparation of Cellular polyHIPE Monoliths Utilizing Vegetable Oil as the Second Phase, a Mixture of HMT and Furfuryl Alcohol as the Hardening Agent and Different Quantities of Cremophor ELP as the Surfactant 9.1. Procedure Furfuryl alcohol at constant concentration was utilized as the hardening agent, in addition to HMT, and different quantities of the surfactant Cremophor ELP were utilized.

The preparation protocol is identical to that of Example 5, apart from the following exceptions:
5 g of furfuryl alcohol were added in addition to the ingredients already described in step a); antifoaming agent was not added, as the presence of furfuryl alcohol visibly limited the aeration of the solution during the mixing;
the quantity of Cremophor ELP was varied in the range 2-10% with respect to the total mass of solution;
the oven temperature in step d) is 85° C.;
in step e), a step of oil extraction with acetone using the Soxhlet for 7 days is added before the drying step at ambient temperature. It should be noted that during the drying step cracks can occur in the monoliths. This cracking can be markedly limited by addition of 5% by mass (with respect to the total mass of solution) of ethylene glycol or 5-10% by mass (with respect to the total mass of solution) of glycerol to the formulation. The formulations are therefore as follows:

| Name of material | TFA2 | TFA4 | TFA6 | TFA8 | TFA10 |
|---|---|---|---|---|---|
| Tannin (g) | 20 | 20 | 20 | 20 | 20 |
| Furfuryl alcohol (g) | 5 | 5 | 5 | 5 | 5 |
| Water (g) | 33.9 | 33.9 | 33.9 | 33.9 | 33.9 |
| PTSA (g) | 0.7 | 0.7 | 0.7 | 0.7 | 0.7 |
| HMT (g) | 1.9 | 1.9 | 1.9 | 1.9 | 1.9 |
| Cremophor ELP (g) | 1.15 | 2.35 | 3.6 | 4.91 | 6.28 |
| Sunflower oil (mL) | 150 | 150 | 150 | 150 | 150 |

For the two polyHIPEs obtained under the conditions described above with 1.15 g of Cremophor ELP, namely 2% by mass, one (TFA2) not containing ethylene glycol and the other (TFA2EG) containing 5% thereof by mass (with respect to the total mass of solution), the formulation conditions are as follows:

| Sample | TFA2 | TFA2EG |
|---|---|---|
| Mass fraction of solids (%) | 40 | 40 |
| Mass fraction of surfactant (%) | 2.0 | 2.0 |
| Volume fraction of second phase (%) | 75 | 75 |
| Mass fraction of ethylene glycol (%) | 0 | 5 |
| Initial pH | 2.5 | 2.5 |
| Speed of rotation in step b) | 500 | 500 |
| Speed of rotation in step c) | 1000 | 1000 |

9.2. Results:

These are given in FIGS. 21 and 22.

The best surfactant concentration range is 2-6% by mass. The monoliths prepared with higher percentages (8 and 10%) tend to crumble during the oil extraction step using a Soxhlet, but also during the subsequent drying; these materials are actually very friable. Those prepared with the lowest surfactant contents are more stable and more homogeneous.

The presence of a little ethylene glycol does not significantly change the results, whether the porosity or the resulting physical properties. On the other hand, the resistance to cracking is very good.

The material TFA2 can be compared to the monolith F75A of Example 1 (see FIGS. 1 and 13). Addition of 2% of Cremophor ELP instead of 5% gives a material with more extensive porosity, and thus having somewhat inferior mechanical properties, and the pores of which are somewhat wider.

The results of the Examples show that:
- all pHs between 2 and 8 can be used, giving materials with different structural and mechanical properties,
- water-in-oil and oil-in-water emulsions alike (the transition from the first to the second occurs by increasing the proportion of oil, but without changing the preparation protocol) give porous monolithic materials with different pore structures,
- all the other parameters of the formulation, without exception, play a part in the adjustment of the porosity in terms of pore volumes, cell diameters and connections between cells, pore connectivity and the resulting physical properties. From this point of view, the nature of the surfactant has a particularly significant effect, thus, on the basis of the processes described, any type of pore structure is henceforth accessible, which is novel for materials originating from tannins: from cross-linked structures to cellular structures, passing via stacks of connected hollow spheres, the ranges of apparent densities (and therefore porosities) accessible are the widest ever attained for porous monoliths originating from tannins, the derived materials, in particular of carbon, retain the same structure and have similar density, while displaying narrower porosity and mechanical properties superior to those of their organic equivalents.

The invention claimed is:

1. A process for the production of porous monolithic materials based on condensed tannins, the process comprising the following steps:
   (a) obtaining a first liquid phase, said first liquid phase being an aqueous solution of condensed tannins;
   (b) obtaining a second phase, said second phase and air being an oil, a volatile solvent not miscible with water, air, a mixture of oil and air, or a mixture of air and a volatile solvent not miscible with water, and said second phase not being miscible with said first liquid phase, and at least one of said first liquid phase and said second phase comprising a surfactant;
   (c) dispersing said second phase in said first liquid phase, in the presence of a hardening agent;
   (d) mixing said first liquid phase and said second phase by stirring until the obtention:
      (i) of a homogeneous and stable emulsion when said second phase is an oil or a volatile solvent not miscible with water; or
      (ii) of a mixture which is macroscopically homogeneous but intermediate between an emulsion and a foam when said second phase is a mixture of oil and air or of air and a volatile solvent not miscible with water; or
      (iii) of a foam when said second phase is air; and
   (e) either,
      (i) carrying out the polymerization of the emulsion or of the emulsion-foam intermediate obtained in step (d)(i) or in step (d)(ii) until the obtention of a solid, washing if necessary and drying said solid; or,
      (ii) carrying out the polymerization and drying said foam obtained in step (d)(iii)
   wherein the concentration of condensed tannins in the aqueous solution of condensed tannins comprises between 20 and 60% by mass of the total mass of condensed tannins and water in the aqueous solution of condensed tannins.

2. The process for the production of porous monolithic materials according to claim 1, wherein either:
   (A) said second phase is a vegetable oil or a volatile solvent not miscible with water and, after hardening of the aqueous phase, extraction of the oil when said second phase is vegetable oil, then drying, a polyHIPE is obtained; or
   (B) said second phase is air and, after hardening of the aqueous phase then drying, a rigid foam is obtained; or
   (C) said second phase is a mixture of vegetable oil and air or of air and a volatile solvent not miscible with water and, after hardening of the aqueous phase, extraction of the oil when said second phase is vegetable oil, then drying, an aerated material is obtained.

3. The process for the production of porous monolithic materials according to claim 2, wherein the aqueous solution of condensed tannins contains an antifoaming agent.

4. The process for the production of porous monolithic materials according to claim 1, wherein the aqueous pH of the solution of condensed tannins is between 2 and 8.

5. The process for the production of porous monolithic materials according to claim 2, wherein said second phase is a vegetable oil or a volatile solvent not miscible with water, the ratio of oil to aqueous solution of condensed tannins or the ratio of volatile solvent to aqueous solution of condensed tannins is 0.4 to 1 and 4 to 1 by volume.

6. The process for the production of porous monolithic materials according to claim 1, wherein the condensed tannins are selected from the group comprising mimosa, pine or quebracho tannins.

7. The process for the production of porous monolithic materials according to claim 1, wherein the surfactant is a non-ionic surfactant.

8. The process for the production of porous monolithic materials according to claim 1, wherein the hardening agent is selected from the group comprising: aldehydes, compounds capable of decomposing into aldehydes, oxazolidines, nitroparaffins, furfuryl alcohol, and any combination of these hardening agents with one another in any proportions.

9. A process for the production of porous monolithic materials based on condensed tannins, the process comprising the following steps:
(a) preparing a first aqueous solution of condensed tannins in water, and optionally adding an antifoaming agent to prepare a polyHIPE, wherein the concentration of condensed tannins in the first aqueous solution of condensed tannins comprises between 20 and 60% by mass of the total mass of condensed tannins and water in the first aqueous solution of condensed tannins;
(b) adjusting the pH of the first aqueous solution of condensed tannins to a value between 2 and 8 to obtain a second solution;
(c) stirring the second solution at a speed between 200 and 2000 rpm until the obtention of a homogeneous solution;
(d) adding a surfactant and maintaining under stirring at a speed between 200 and 2000 rpm until the obtention of another homogeneous solution;
(e) incorporating the vegetable oil dropwise into the homogeneous solution obtained in step (d), while maintaining stirring at a speed between 200 and 2000 rpm until the obtention of a stable and homogeneous emulsion;
(f) incorporating a hardening agent halfway through step (e) and continuing stirring;
(g) carrying out polymerization at a temperature greater than ambient temperature of between 40 and 90° C., until the obtention of a solid emulsion;
(h) washing the solid emulsion obtained in the previous step with an organic solvent to obtain a polyHIPE or a polyHIPE-type monolith; and
(i) drying the polyHIPE or polyHIPE-type monolith.

* * * * *